(12) United States Patent  (10) Patent No.: US 9,724,208 B2
Robinson et al.  (45) Date of Patent: Aug. 8, 2017

(54) EXPANDABLE VERTEBRAL BODY REPLACEMENT DEVICE, SYSTEM, AND METHODS

(71) Applicants: James C. Robinson, Atlanta, GA (US); John E. Pendleton, Atlanta, GA (US)

(72) Inventors: James C. Robinson, Atlanta, GA (US); John E. Pendleton, Atlanta, GA (US)

(73) Assignee: SPECTRUM SPINE IP HOLDINGS, LLC, Atlanta, GA (US)

( * ) Notice: Subject to any disclaimer, the term of this patent is extended or adjusted under 35 U.S.C. 154(b) by 0 days.

(21) Appl. No.: 14/830,869

(22) Filed: Aug. 20, 2015

(65) Prior Publication Data

US 2016/0045327 A1  Feb. 18, 2016

Related U.S. Application Data

(63) Continuation of application No. 14/216,893, filed on Mar. 17, 2014, now abandoned, which is a (Continued)

(51) Int. Cl.
*A61F 2/44* (2006.01)
*A61F 2/46* (2006.01)
(Continued)

(52) U.S. Cl.
CPC ............... *A61F 2/447* (2013.01); *A61F 2/44* (2013.01); *A61F 2/4455* (2013.01);
(Continued)

(58) Field of Classification Search
CPC ........ A61F 2/44; A61F 2/442; A61F 2/30965; A61F 2/4465; A61F 2/4684; A61F 2/4611; A61F 2/4455; A61F 2/447; A61F 2002/4475; A61F 2002/3024; A61F 2002/30131; A61F 2002/30235; A61F 2002/30433; A61F 2002/30471; A61F 2002/30481; A61F 2002/30494; A61F 2002/30583; A61F 2002/30497; A61F 2002/3052; A61F 2002/30; A61F 2002/523; A61F 2002/30556; A61F 2002/30579; A61F 2002/30601; A61F 2002/3078;
(Continued)

(56) References Cited

U.S. PATENT DOCUMENTS 6,176,881 B1  1/2001  Schar et al.
6,527,803 B1 *  3/2003  Crozet .................. A61F 2/4455
                                                          606/31
(Continued)

FOREIGN PATENT DOCUMENTS

WO   WO0023013 A1   4/2000
WO   WO2009151734 A1  12/2009

*Primary Examiner* — Pedro Philogene
(74) *Attorney, Agent, or Firm* — FisherBroyles, LLP; Anthony J. DoVale

(57) ABSTRACT

An expandable vertebral body replacement is presented. The device has an inner and outer housing longitudinally moveable on one-another which locks in place using a retention member. This can be locked or fortified by several described options. Also presented is a method for expanding said device embodiments and a system for an expandable vertebral body replacement.

18 Claims, 49 Drawing Sheets

Related U.S. Application Data continuation-in-part of application No. 14/216,513, filed on Mar. 17, 2014, now abandoned.

(60) Provisional application No. 61/802,360, filed on Mar. 15, 2013.

(51) Int. Cl.
  *A61F 2/30* (2006.01)
  *A61B 17/02* (2006.01)
  *A61F 2/28* (2006.01)

(52) U.S. Cl.
  CPC ..... *A61F 2/4611* (2013.01); *A61B 2017/0256* (2013.01); *A61F 2002/2835* (2013.01); *A61F 2002/3024* (2013.01); *A61F 2002/3052* (2013.01); *A61F 2002/3078* (2013.01); *A61F 2002/30131* (2013.01); *A61F 2002/30235* (2013.01); *A61F 2002/30433* (2013.01); *A61F 2002/30471* (2013.01); *A61F 2002/30481* (2013.01); *A61F 2002/30494* (2013.01); *A61F 2002/30497* (2013.01); *A61F 2002/30523* (2013.01); *A61F 2002/30538* (2013.01); *A61F 2002/30556* (2013.01); *A61F 2002/30579* (2013.01); *A61F 2002/30601* (2013.01); *A61F 2002/30841* (2013.01); *A61F 2002/30904* (2013.01); *A61F 2002/4475* (2013.01)

(58) Field of Classification Search
  CPC .. A61F 2002/30841; A61F 2002/30904; A61F 2002/2835; A61B 2017/0256
  USPC .............................. 623/17.11–17.16; 606/246
  See application file for complete search history.

(56) References Cited

U.S. PATENT DOCUMENTS

| | | | |
|---|---|---|---|
| 6,648,917 B2 | 11/2003 | Gerbec et al. | |
| 7,544,208 B1 | 6/2009 | Mueller | |
| 7,758,648 B2 | 7/2010 | Castleman et al. | |
| 7,879,096 B2 | 2/2011 | Dickson et al. | |
| 8,187,332 B2* | 5/2012 | McLuen | A61F 2/4455 623/17.16 |
| 2003/0176925 A1* | 9/2003 | Paponneau | A61F 2/44 623/17.16 |
| 2003/0191535 A1* | 10/2003 | Castro | A61F 2/4465 623/17.16 |
| 2004/0162618 A1 | 8/2004 | Mujwid et al. | |
| 2006/0200244 A1 | 9/2006 | Assaker | |
| 2007/0255408 A1 | 11/2007 | Castleman et al. | |
| 2007/0255409 A1 | 11/2007 | Dickson et al. | |
| 2007/0255410 A1 | 11/2007 | Dickson et al. | |
| 2008/0288071 A1 | 11/2008 | Biyani | |
| 2009/0118765 A1 | 5/2009 | Mueller | |
| 2009/0138089 A1 | 5/2009 | Doubler et al. | |
| 2009/0164017 A1 | 6/2009 | Sommerich et al. | |
| 2010/0249934 A1 | 9/2010 | Melkent | |
| 2010/0280614 A1* | 11/2010 | Castleman | A61F 2/4611 623/17.11 |
| 2011/0015746 A1 | 1/2011 | Melkent et al. | |
| 2011/0087328 A1 | 4/2011 | Dickson et al. | |
| 2011/0098820 A1* | 4/2011 | Blackwell | A61F 2/30734 623/17.16 |
| 2012/0095561 A1* | 4/2012 | Voisard | A61F 2/442 623/17.16 |
| 2012/0109307 A1* | 5/2012 | Drochner | A61F 2/4455 623/17.16 |
| 2012/0226356 A1 | 9/2012 | Hirschl | |

* cited by examiner

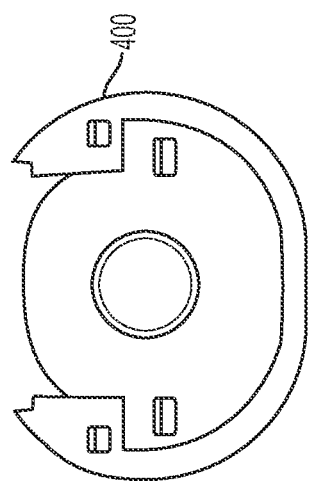
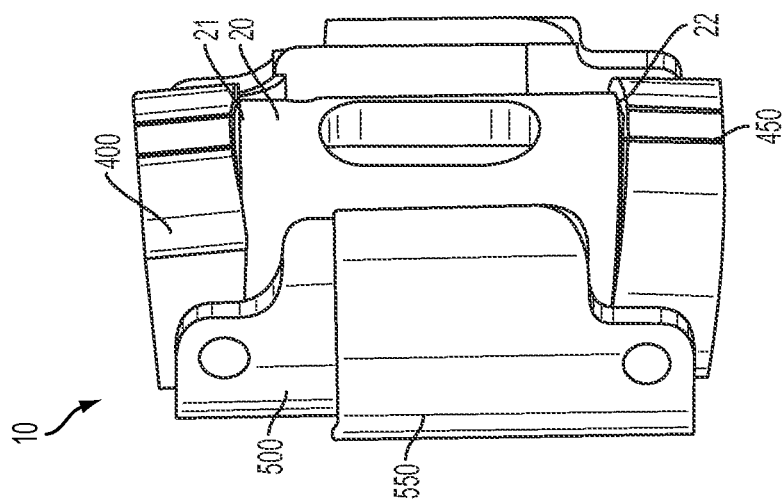

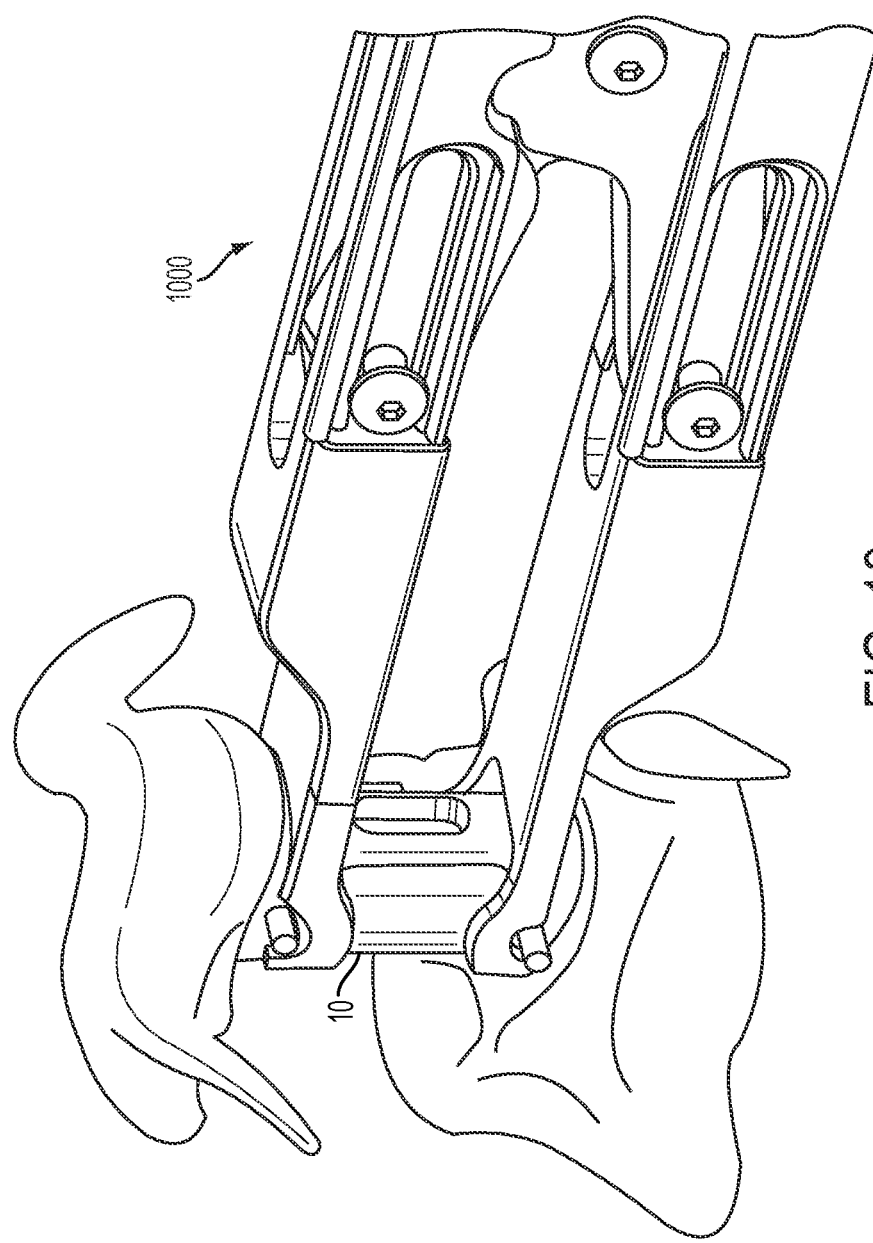

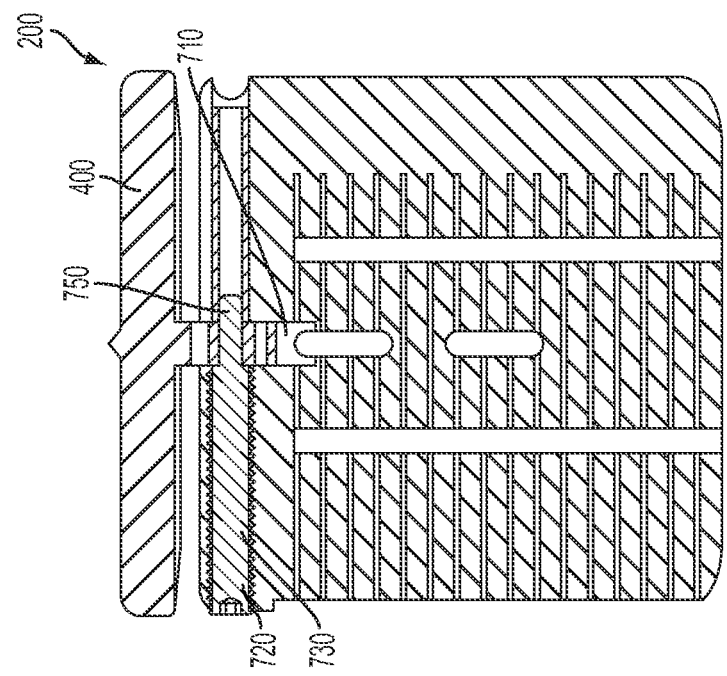
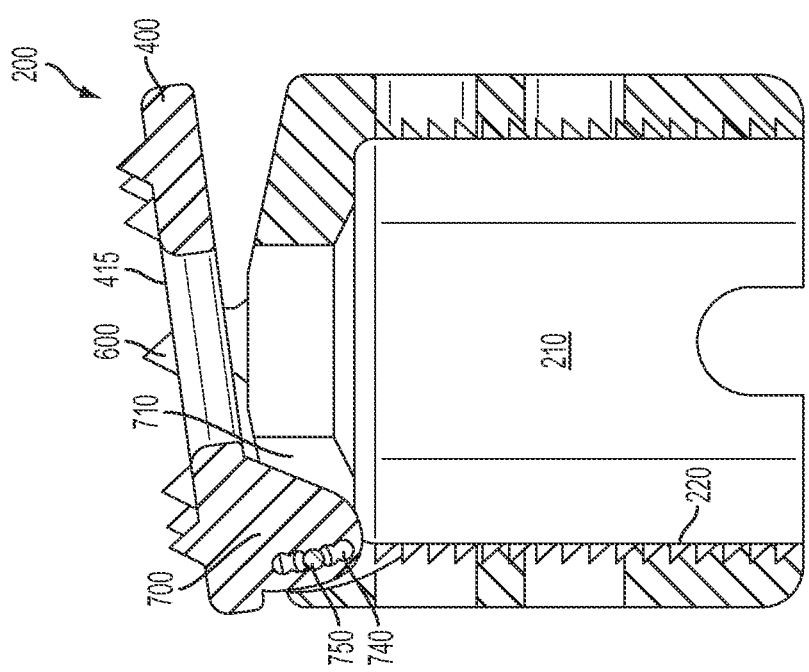

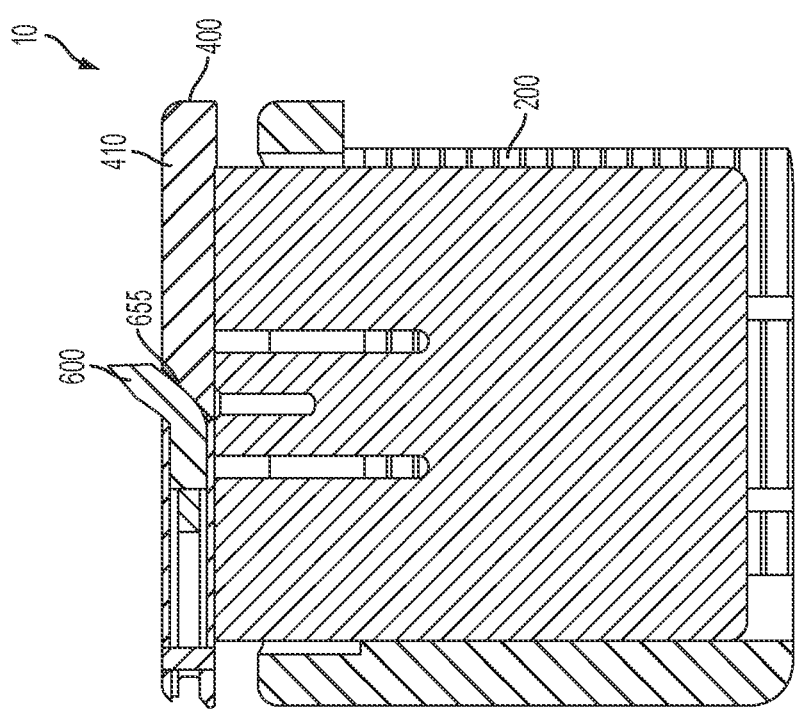

EXPANDABLE VERTEBRAL BODY REPLACEMENT DEVICE, SYSTEM, AND METHODS

CONTINUITY

This application claims priority to and the benefit of U.S. Provisional Patent Application No. 61/802,360, filed on Mar. 15, 2013, U.S. Utility application Ser. No. 14/216,513, filed on Mar. 17, 2014, and co-pending U.S. Utility application Ser. No. 14/216,893, filed on Mar. 17, 2014, the contents of which are incorporated herein in their entirety.

FIELD OF THE INVENTION

This invention relates generally to spinal surgery, and more particularly to devices and methods of stabilization of the spine following removal of a vertebral body, and replacing it with an expandable construct to stabilize the adjacent bones and provide a corridor between them for fusion purposes.

BACKGROUND OF THE INVENTION

Damage to a vertebral bone, often due to a traumatic fracture or due to invasion of the bone by tumor, at times requires removal of the vertebral body. This operation is known as a corpectomy. Following corpectomy, the resultant gap is generally filled in by a weight bearing support know as a Vertebral Body Replacement (VBR). This helps to restore and maintain the proper spacing between the adjacent bones, and often provides an area for placing graft material to span the adjacent bones in order to allow a fusion to take place.

VBRs may be sized to fit the gap, or be expandable over a range. The expandable VBRs currently available have significant limitations. These include the inability to adequately pack graft material in the channel within them post-expansion, a lack of a satisfactory match of the top and bottom of the implant to the adjacent bone surfaces, and expansion mechanisms that are complex, or take an inordinate amount of time to actuate. A need remains for an implant and surgical technique that will overcome these shortfalls.

SUMMARY

Presented herein is an expandable VBR device for use in spinal surgery following a vertebral corpectomy in the cervical, thoracic, or lumbar spine. The VBR device comprises an inner housing and an outer housing. The inner housing and outer housing can move in relation to one another in the longitudinal direction to increase or reduce the height of the VBR device. The VBR device can be expanded within a range from the first, unexpanded position, to a second fully expanded position or substantially any position therebetween.

A system is also presented, the system comprising a VBR device and a VBR expansion tool. In one exemplified aspect, the VBR expansion tool comprises an actuation member coupled to a leveling member. In use, compression of the handles of the actuation member from the first position to the second position, moves the leveling members from a position substantially adjacent one another to a separated position, moving the expandable VBR device from the unexpanded position to the expanded position.

A method of placing an expandable VBR into a corpectomy defect, and expanding the height of the device using a VBR expansion tool is also presented. The method comprises, accessing the desired motion segment, removing the desired vertebral body, positioning the expandable VBR device in place of the removed vertebral body, expanding the expandable VBR device, and fixing the expandable VBR device in the expanded position. The method can also comprise fixing the lordotic angle of the upper and/or lower bone contact members. In another aspect, the method also comprises packing the graft cavity with bone growth promoting materials.

Related methods are also provided. Other apparatuses, methods, systems, features, and advantages of the expandable VBR device and the method of its use will be or become apparent to one with skill in the art upon examination of the following figures and detailed description. It is intended that all such additional apparatuses, methods, systems, features, and advantages be included within this description, be within the scope of the expandable VBR device and the method of its use, and be protected by the accompanying claims.

DESCRIPTION OF THE FIGURES

The accompanying drawings, which are incorporated in and constitute a part of this specification, illustrate certain aspects of the instant invention and together with the description, serve to explain, without limitation, the principles of the invention. Like reference characters used therein indicate like parts throughout the several drawings.

FIG. 7 is a perspective view of the VBR device of FIG. 6 in an expanded position;

FIG. 8 is a top plan view of the VBR device of FIG. 6;

FIG. 13 is a perspective view of the VBR device of FIG. 6, showing the VBR device with a VBR expansion tool;

FIG. 37 is a front cut-away view of the outer housing of FIG. 31, cut along line 35-35 of FIG. 33;

FIG. 38 is a front cut-away view of the outer housing of FIG. 31, cut along line 38-38 of FIG. 36;

FIG. 67 is a cut-away side view of the VBR device of FIG. 59, cut along line 67-67 of FIG. 66;

DESCRIPTION OF THE INVENTION

Figure 1:
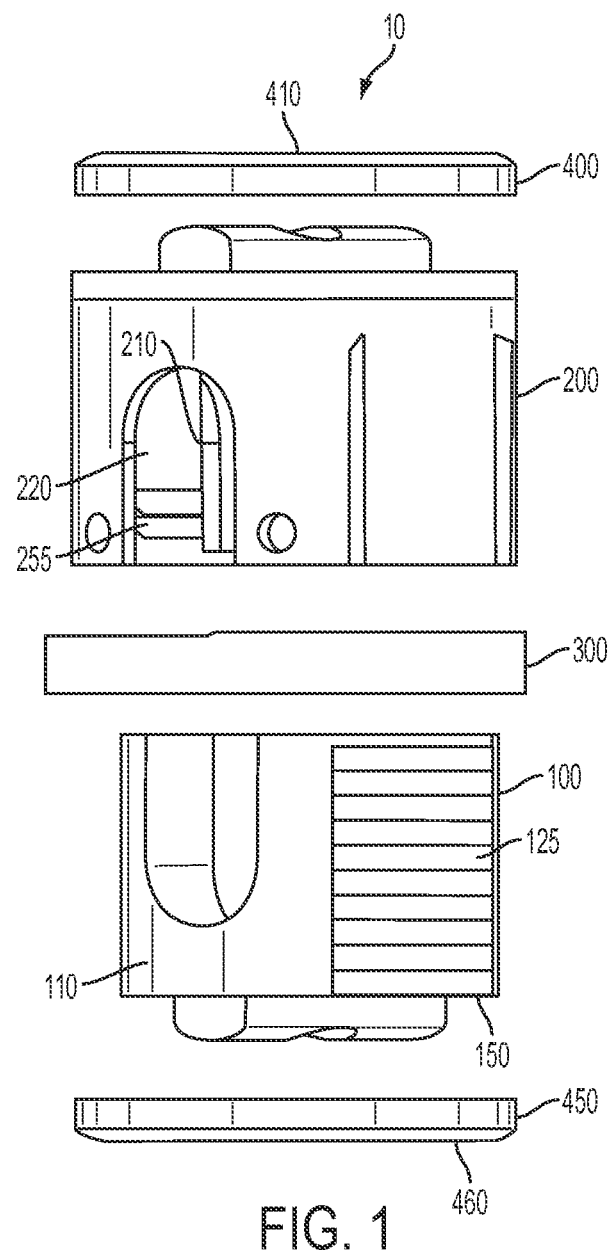
FIG. 1 is a partially exploded front perspective view of one aspect of a VBR device.
Figure 2:
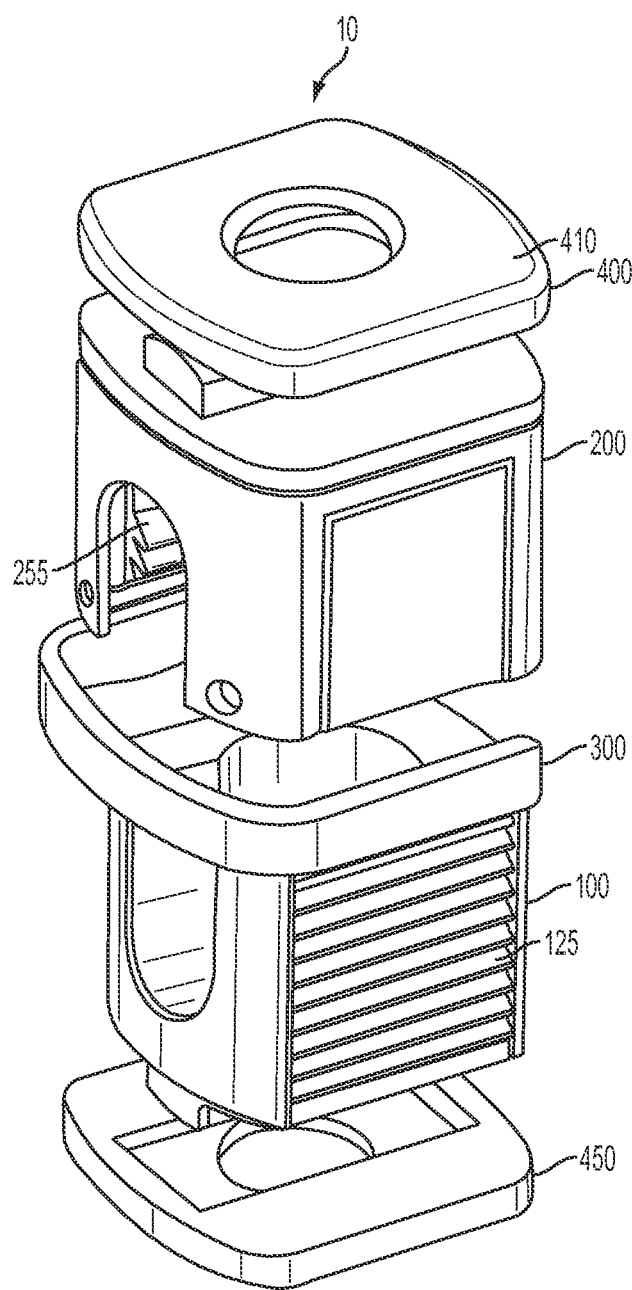
FIG. 2 is a partially exploded perspective view of the VBR device of FIG. 1.
Figure 5:
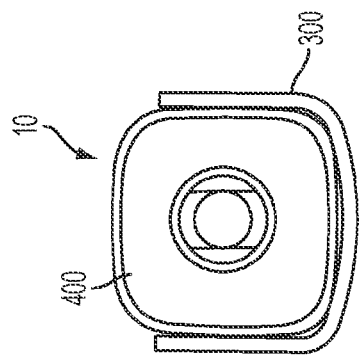
FIG. 5 is a top plan view of the VBR device of FIG. 1.
Figure 4:
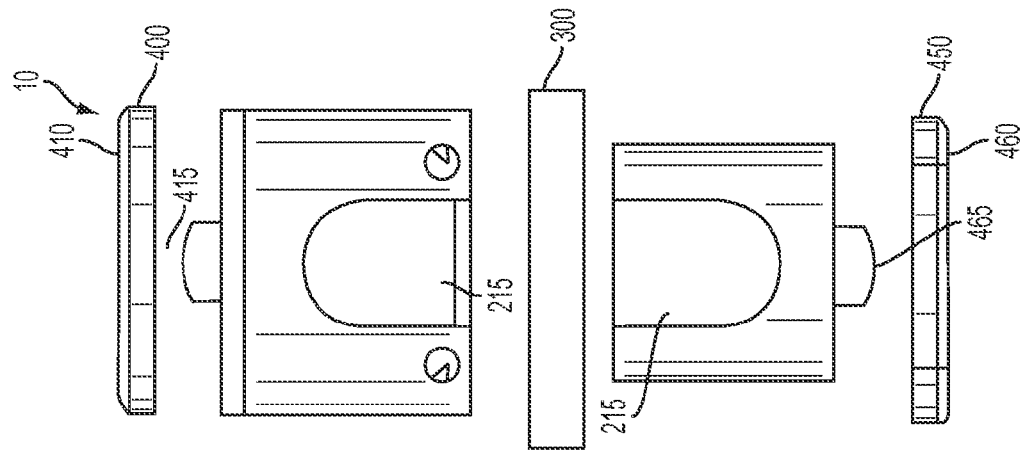
FIG. 4 is a partially exploded front view of the VBR device of FIG. 1.
Figure 3:
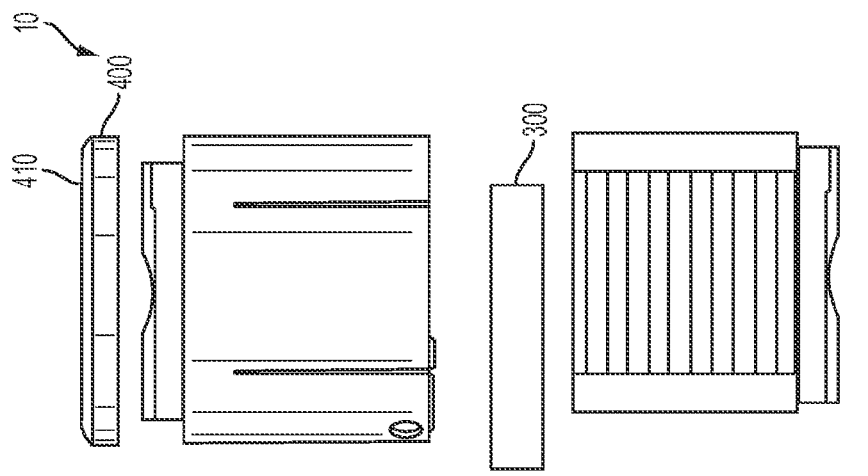
FIG. 3 is a partially exploded side view of the VBR device of FIG. 1.
Figure 6:
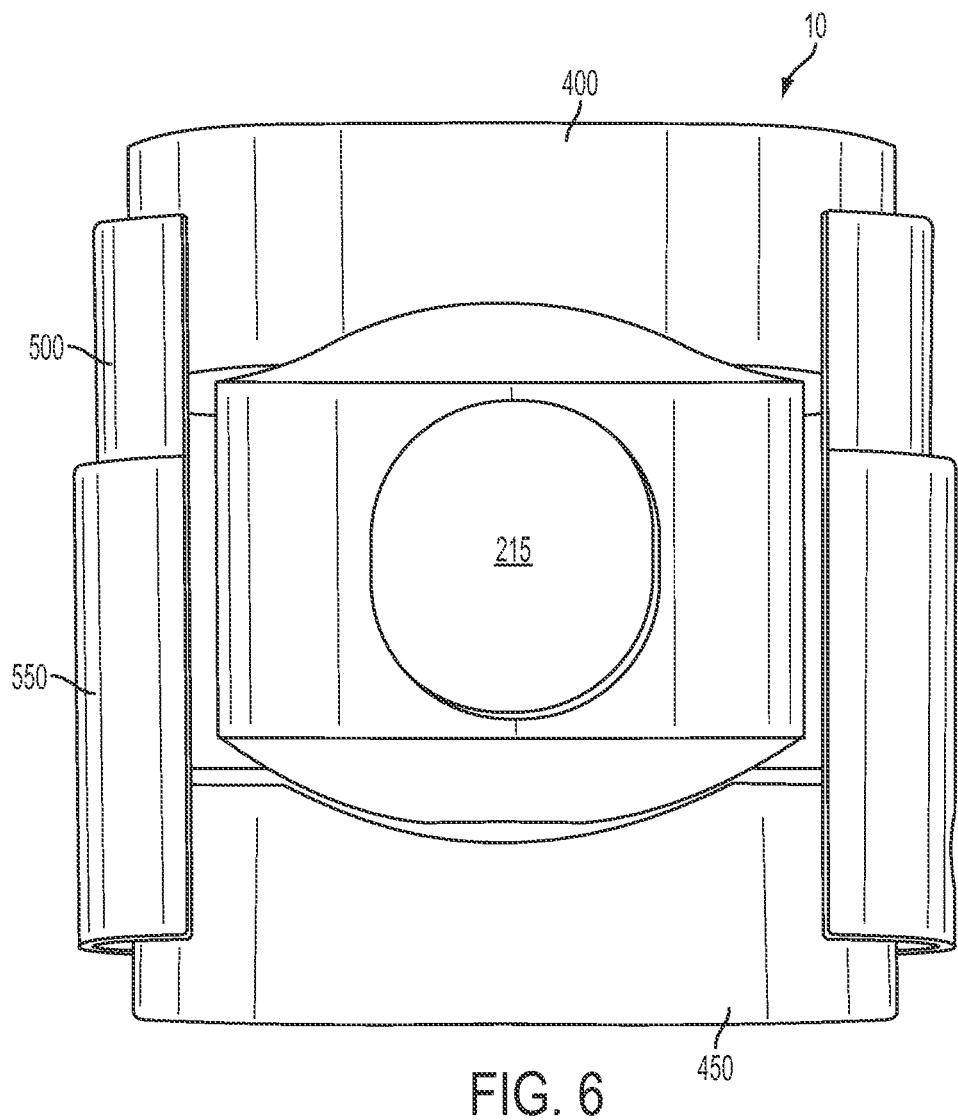
FIG. 6 is a front view of another aspect of a VBR device in the unexpanded position.
Figure 9:
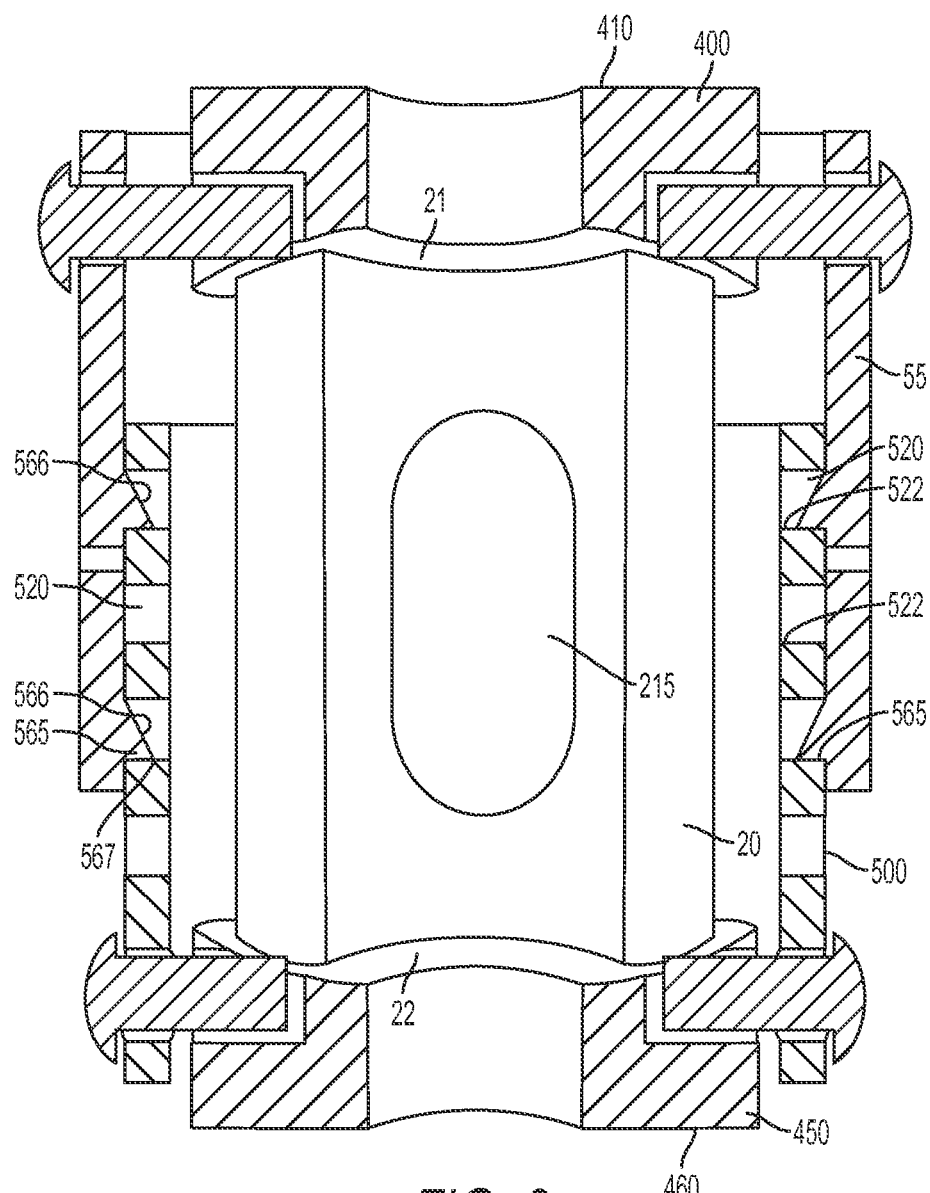
FIG. 9 is a cut away front view of the VBR device of FIG. 6, showing a ratchet mechanism for restraining the VBR from moving into the retracted position from the expanded position.
Figure 11:
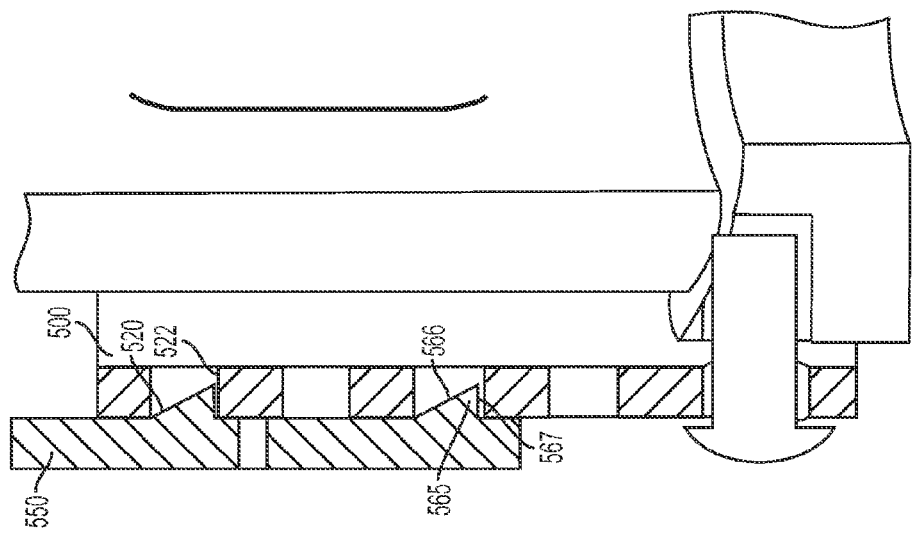
FIG. 11 is a cutaway view of the engagement of the inner and outer sleeve of the VBR device of FIG. 10.
Figure 10:
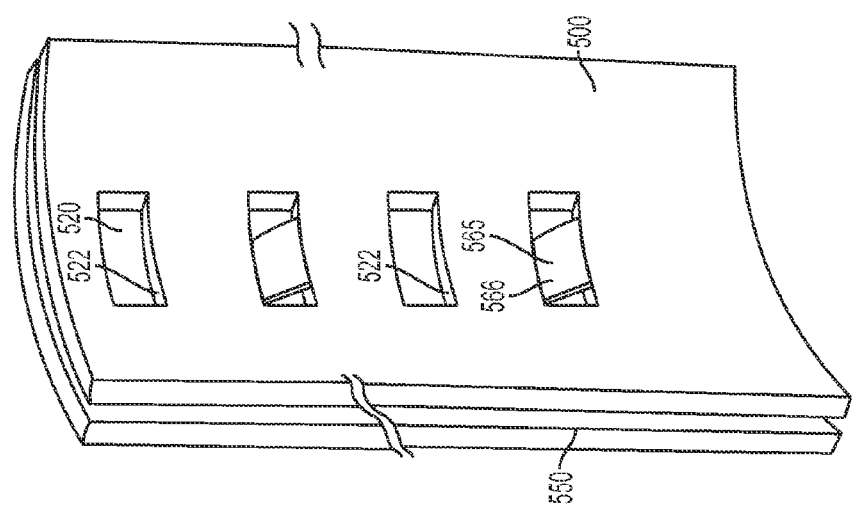
FIG. 10 is a partial perspective view of an interior wall of an inner sleeve of the VBR device of FIG. 6, showing the relationship of a tooth positioned on the interior wall of the outer sleeve with a recess defined in the exterior wall of the inner sleeve.
Figure 12:
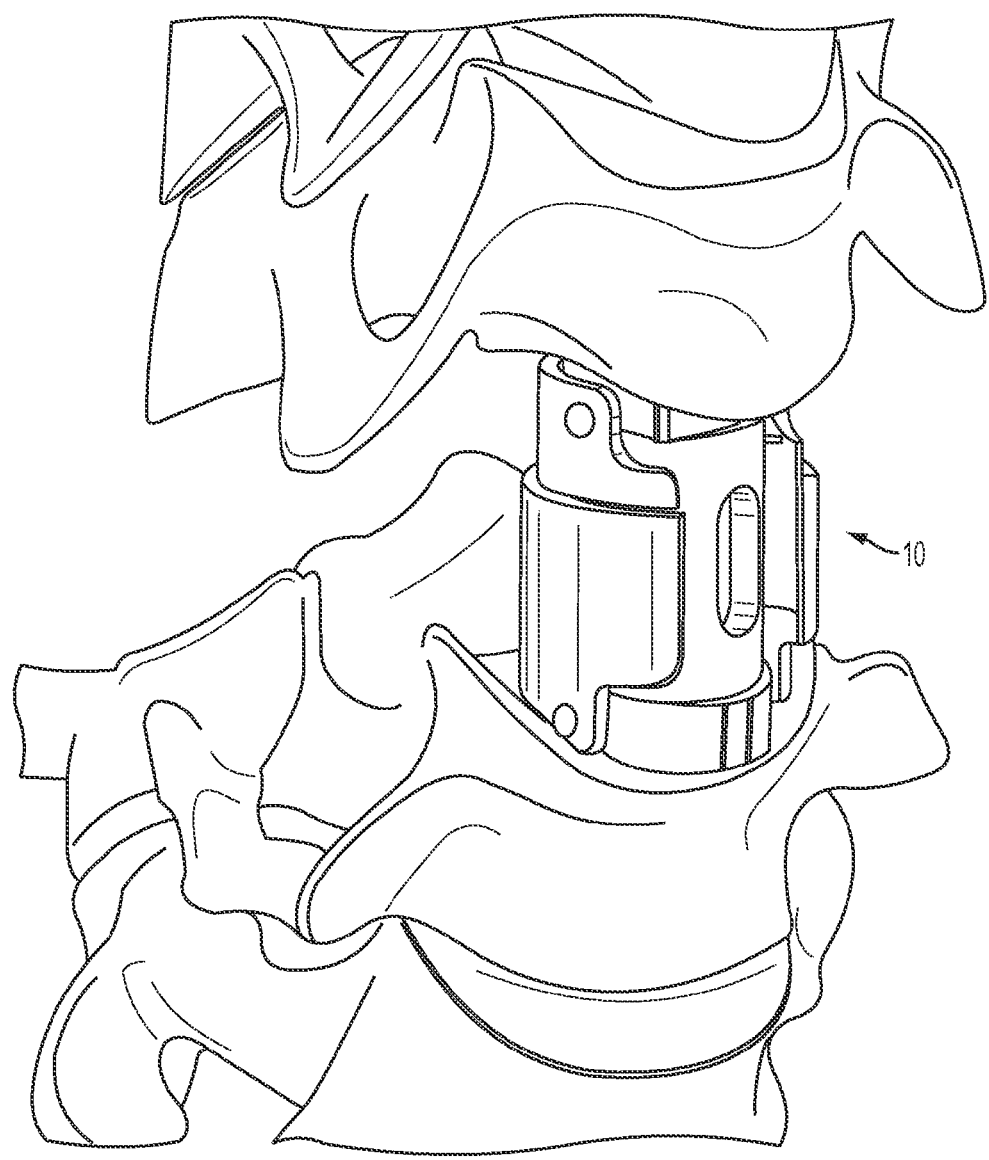
FIG. 12 is a perspective view of the VBR device of FIG. 6, showing the VBR device positioned between two vertebrae.
Figure 15:
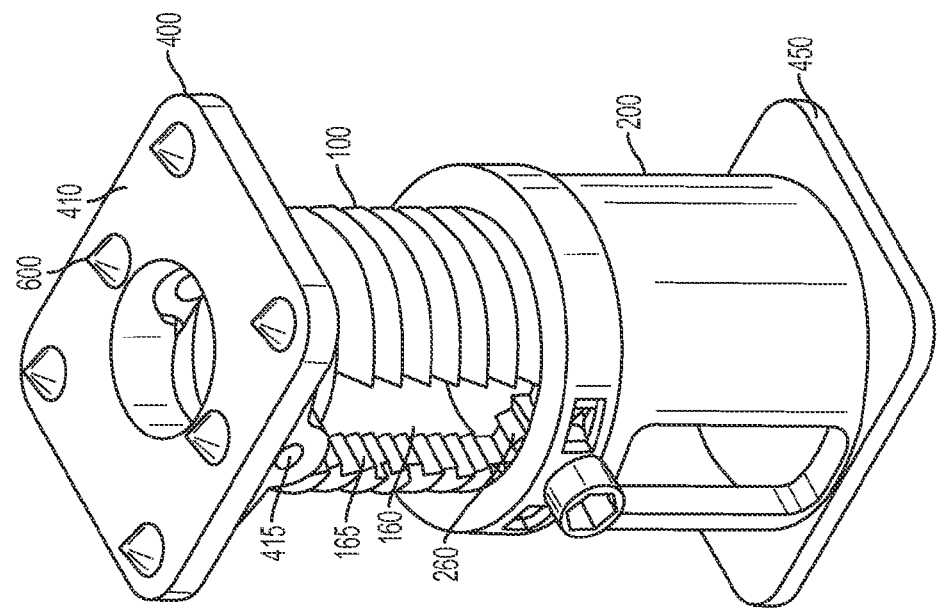
FIG. 15 is a perspective view of the VBR device of FIG. 14.
Figure 14:
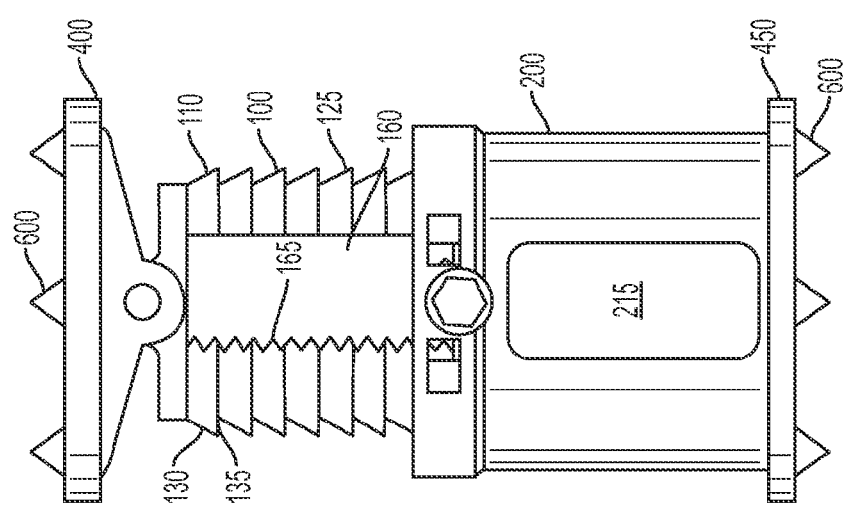
FIG. 14 is a front view of one aspect of a VBR device showing an inner housing and an outer housing.
Figure 17:
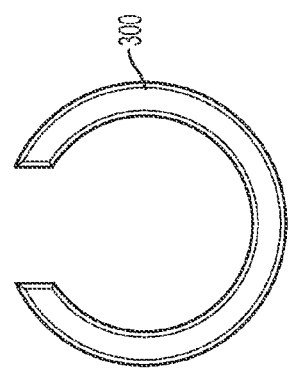
FIG. 17 is a top plan view of a retention member.
Figure 18:
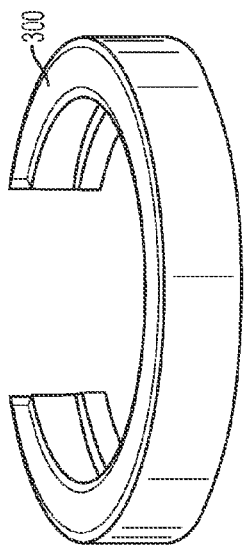
FIG. 18 is a perspective view of the retention member of FIG. 17.
Figure 16:
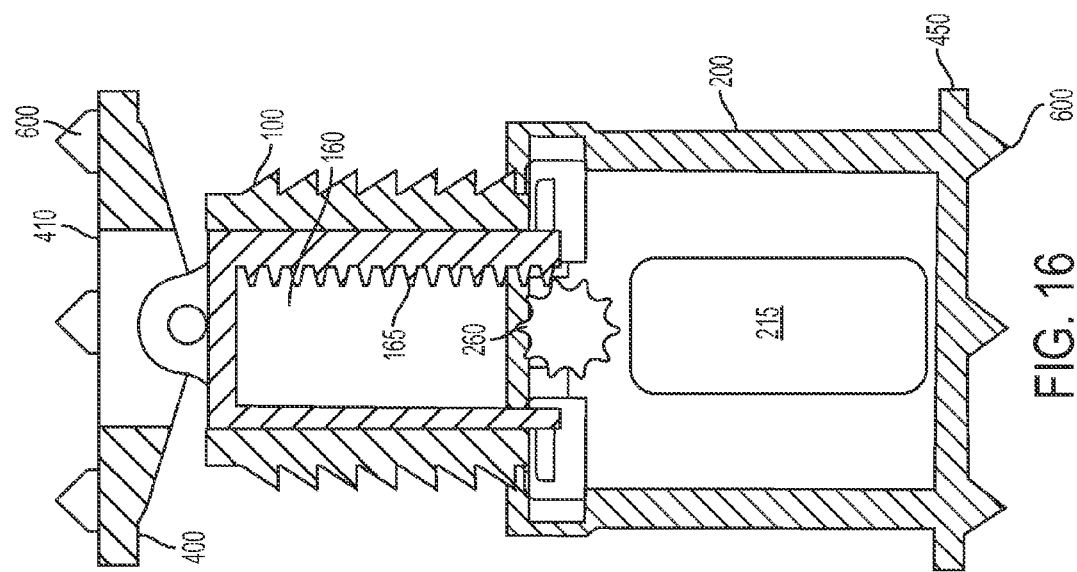
FIG. 16 is a cut away front view of the VBR device of FIG. 14, showing gear engaged with a toothed inner surface of the inner housing.
Figure 19:
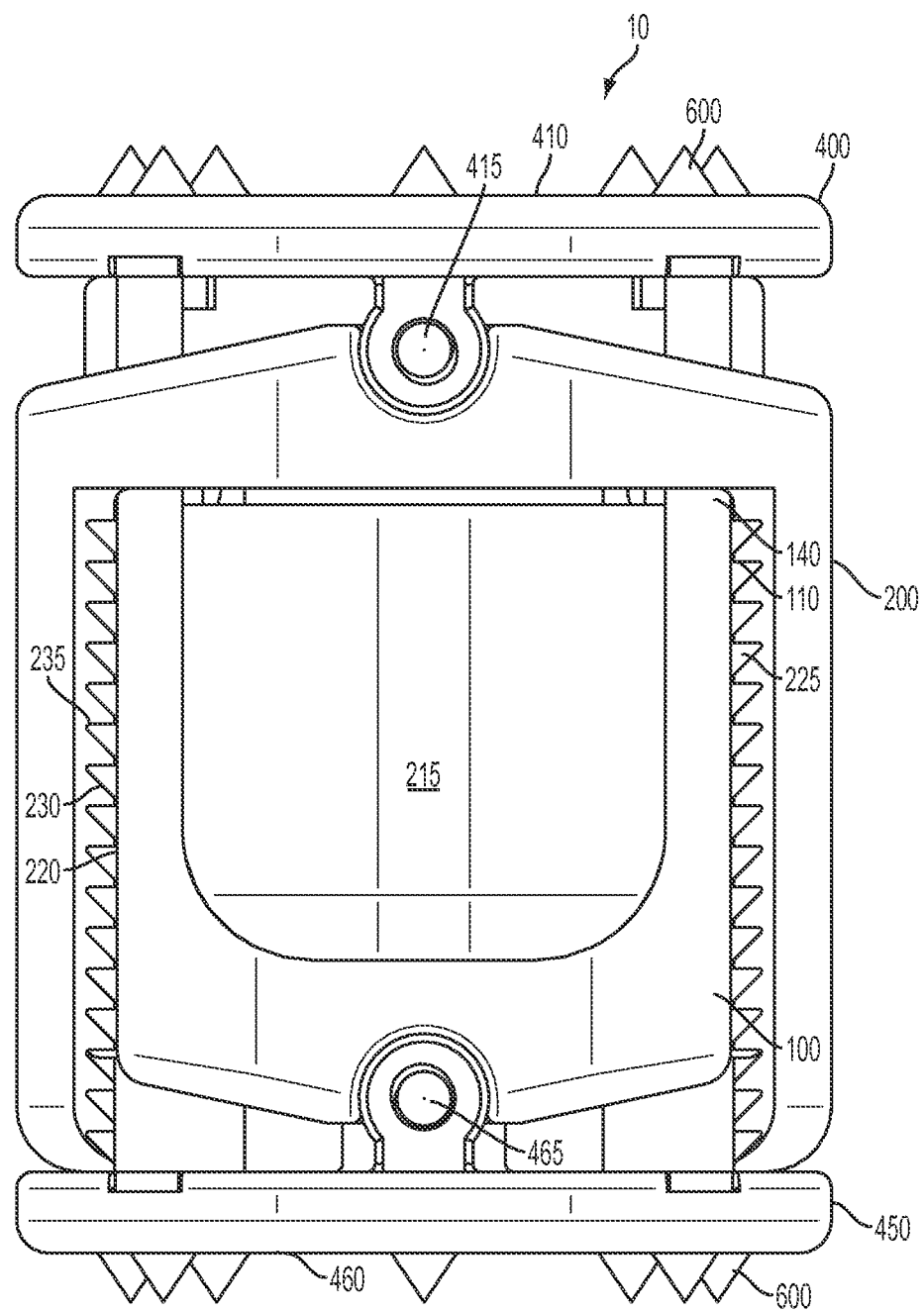
FIG. 19 is a front view of one aspect of a VBR device in the unexpanded position.

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

The following description of the invention is provided as an enabling teaching of the invention in its best, currently known aspect. Those skilled in the relevant art will recognize that many changes can be made to the aspects described, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used herein, the singular forms "a," "an" and "the" include plural referents unless the context clearly dictates otherwise. Thus, for example, reference to a "plate" includes aspects having two or more plates unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Terms used herein, such as "exemplary" or "exemplified," are not meant to show preference, but rather to explain that the aspect discussed thereafter is merely one example of the aspect presented.

Additionally, as used herein, relative terms, such as "substantially", "generally", "approximately", and the like, are utilized herein to represent an inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

In one aspect, presented herein is an expandable VBR device 10 for use in spinal surgery following a vertebral corpectomy in the cervical, thoracic, or lumbar spine. The VBR device comprises an inner housing 100 and an outer housing 200. The inner housing 100 and outer housing 200 can move in relation to one another in the longitudinal direction to increase or reduce the height of the VBR device 10. In one exemplified aspect, the outer housing defines in interior cavity 210 within which the inner housing can nest in the unexpanded position. In another aspect, the inner housing 100 and outer housing 200, together, define a graft cavity 215 for the placement of bone graft material, to include, but not limited to, allograft, bone substitute, or other biocompatible bone growth promoting materials.

The VBR device can be expanded within a range from the first, unexpanded position, to a second fully expanded position or substantially any position therebetween. In an exemplified aspect, an interior surface 220 of the outer housing 200 comprises a toothed surface 225. A toothed surface can be positive, such as protrusions, or negative, such as recesses. In one aspect, the exterior surface 110 of the inner housing 100 comprises a toothed surface 125, as well. Each tooth can comprise a cam 130, 230 surface and a flat surface 135, 235. In one aspect, the toothed surfaces are complimentarily opposite, meaning that in the expanding direction, the cam surface 230 of a tooth 225 on the outer housing 200 mates with the cam surface 130 of a tooth 125 on the inner housing 100 and, in the retracting direction, the flat surface 235 of a tooth 230 on the outer housing 200 engages the flat surface 135 of a tooth 125 on the inner housing 100. This relationship permits the two housings to move in the expanding direction in a ratcheting manner, but prevents the two housings to move in the retracting direction.

In another exemplified aspect, each tooth 125, 225 can comprise two cam surfaces 130, 230, without a flat surface. Additionally, the VBR device can comprise a retention member 300 configured to engage at least a portion of the toothed surface of the inner housing to prevent longitudinal up and down movement of the outer housing with respect to the inner housing. In one aspect, the retention member can be a u-shaped member sized to horizontally slide around at least at least portions the exterior surface 110 of the inner housing 100.

In still another exemplified aspect, the inner housing may define a window 160 having a toothed edge portion 165. In this aspect, a gear 260 can be positioned on the outer housing 200 configured to engage the toothed edge portion 165 of the window 160 of the inner housing 100. In one aspect, the exterior surface 110 of the inner housing may comprise a toothed surface 125. The VBR device can also comprise a retention member 300 configured to engage the exterior surface of the inner housing to restrict movement of the inner housing with respect to the outer housing. The retention member can be a c-ring configured to at least partially wrap around the inner housing and engage at least one of the teeth on the external surface of the inner housing.

Figure 20:
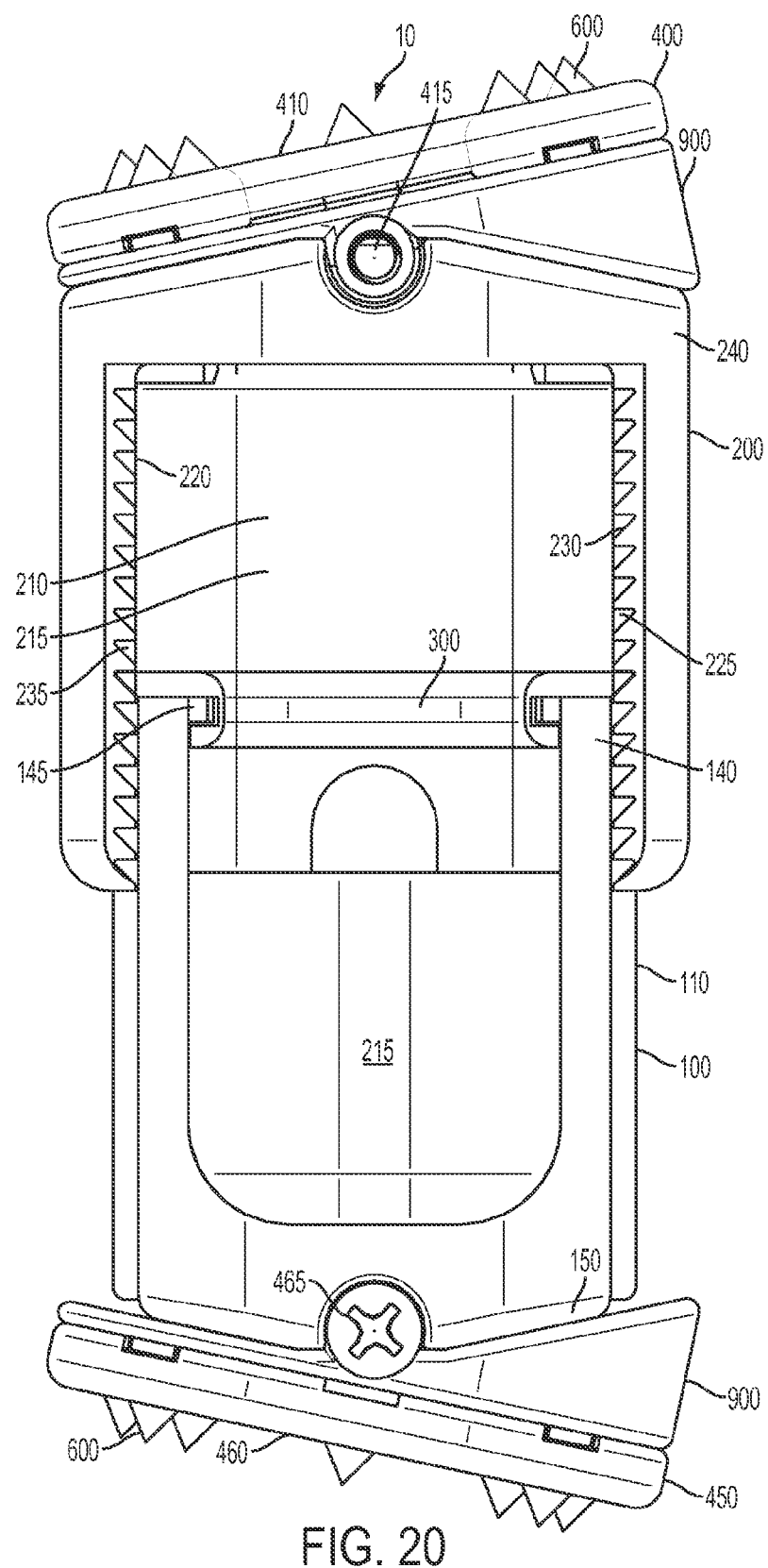
FIG. 20 is a front view of the VBR device of FIG. 19 in the expanded position, illustrating wedge members angling the bone contact members.
Figure 21:
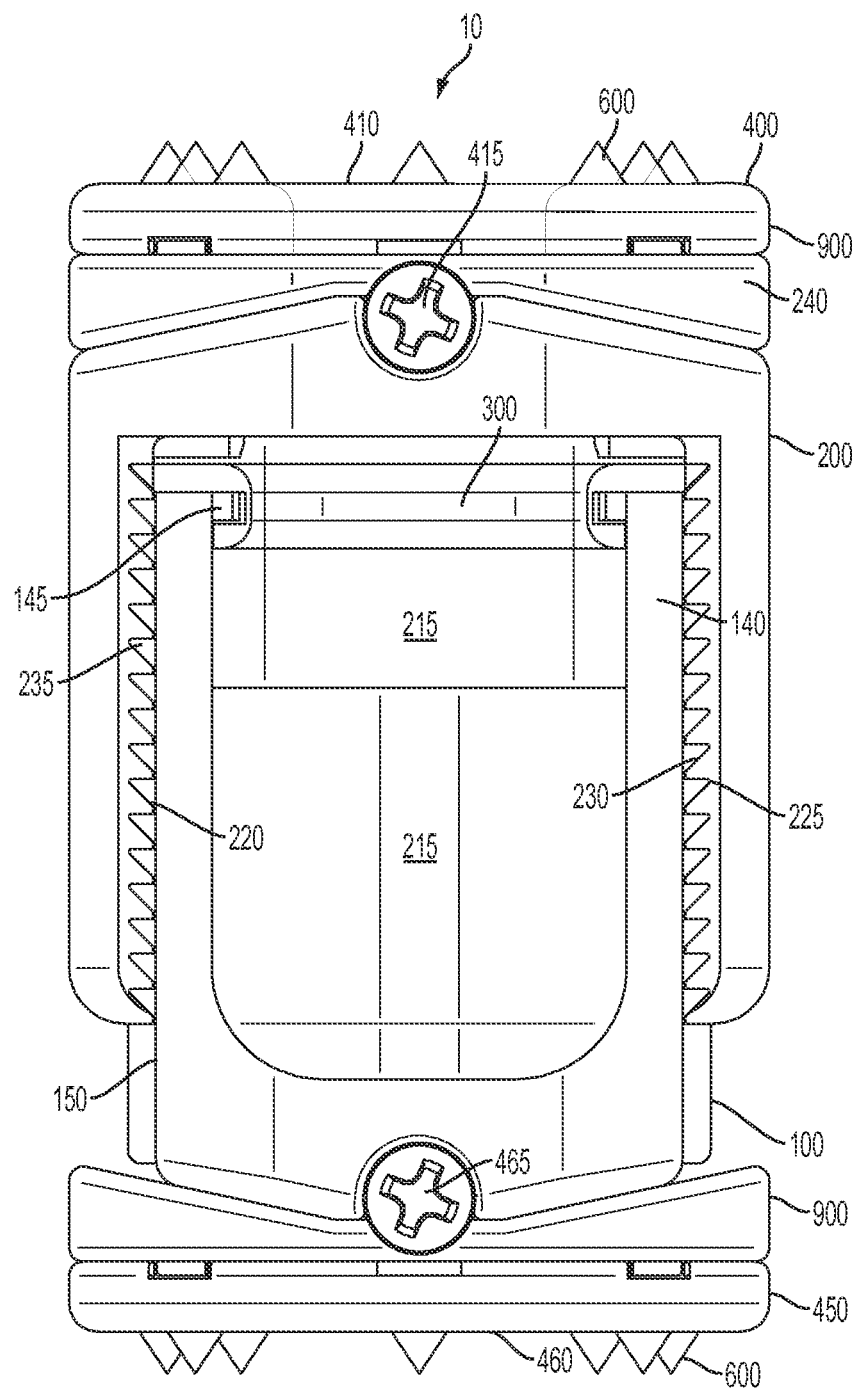
FIG. 21 is a front view of the VBR device of FIG. 19 in a partially expanded position, illustrating wedge members positioned to keep the bone contact members in a flat position.
Figure 22:
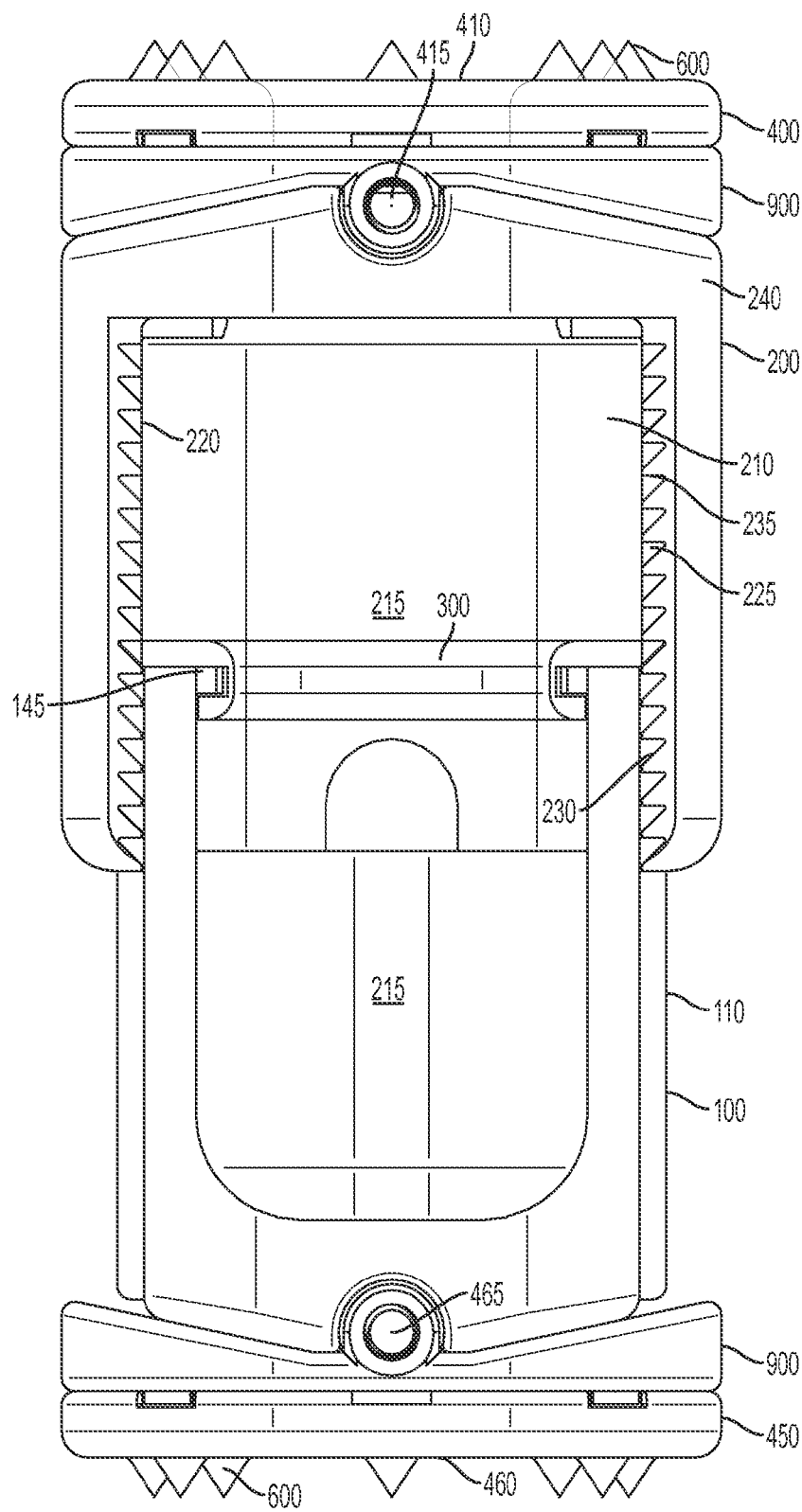
FIG. 22 is a front view of the VBR device of FIG. 21 in the expanded position.
Figure 23:
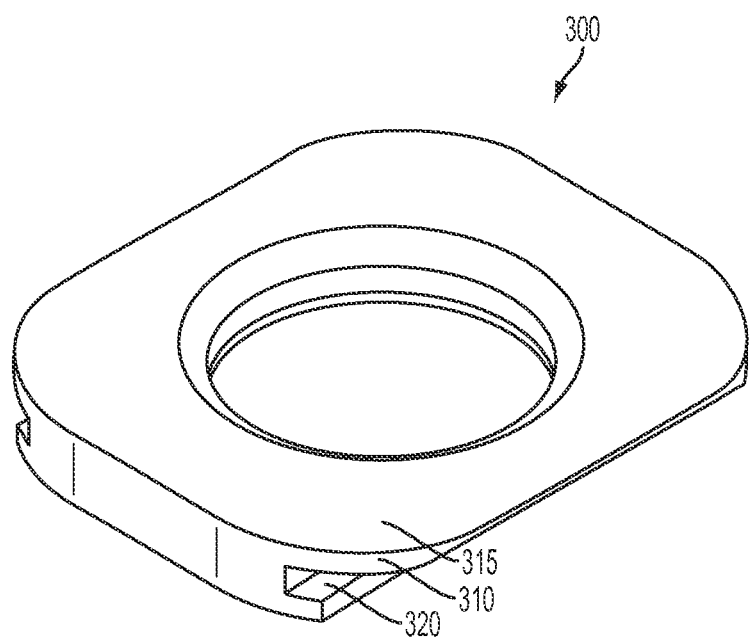
FIG. 23 is a perspective view of one aspect of a retention member for use with a VBR device.
Figure 24:
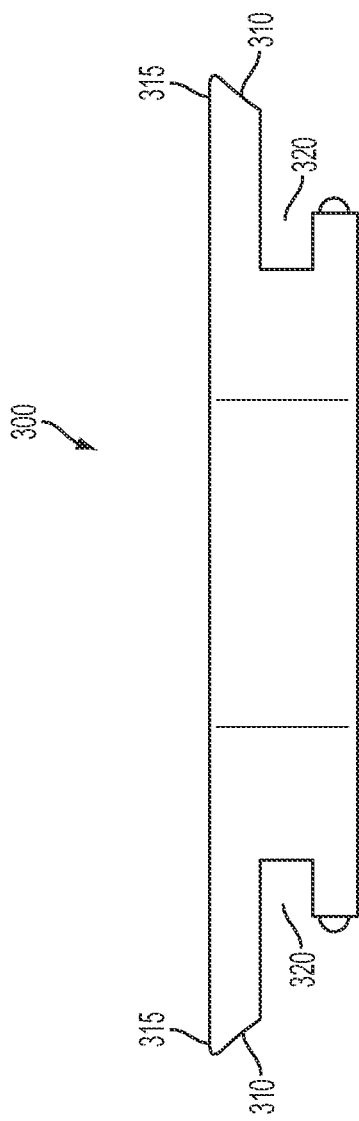
FIG. 24 is a front elevational view of the retention member of FIG. 23.

The retention member 300 can have, for example, edge portion 310 that are cammed and complimentary to the toothed surfaces 225 of the interior surface 220 of the outer housing 200. However, since the toothed surfaces are generally sloped, the edge portion of the retention member need not be angled, sloped, or cammed. It is also contemplated that the edge portion 310 of the retention member have a top surface 315 that is substantially flat in order to retain the flat portion 235 of the toothed surfaces 225 of the interior surface 220 of the outer housing 200. In still another aspect, the retention member can be removably attached to a portion of the inner housing. As illustrated in FIG. 20, the top portion 140 of the inner housing 100 can comprise a tongue 145 and the edge portion 310 of the retention member 300 can comprise a corresponding groove 320 to enable the retention member to slide into position at a top portion of the inner housing. In this aspect, when the retention member is positioned in engagement with the inner housing, the outer housing is prevented from retracting downward toward the unexpanded position, while still being able to ratchet in the upward direction toward the expanded position. When the retention member is moved out of engagement with the inner housing, the outer housing can therefore move in either direction substantially unimpeded.

In an exemplified aspect, the VBR device comprises an upper bone contact member 400 and a lower bone contact member 450. The upper bone contact member 400 has an upper bone contact surface 410 configured for contact with a lower portion of a first vertebra. The lower bone contact member 450 has a lower bone contact surface 460 configured for contact with an upper portion of a second vertebra. One or both of the upper and lower bone contact members can be substantially planar. In one aspect, the upper bone contact member can be pivotally connected to a portion of the top portion 240 of the outer housing. The pivot point 415 can, for example, be in substantially the center of the of the upper bone contact member, enable the upper bone contact member to angulate in either the anterior or posterior direction. The function permits the VBR device to adapt to the anatomy of the patient. As can be appreciated, the lower bone contact member 450 can be pivotally connected to a portion of the bottom portion 150 of the inner housing 100. The pivot point 465 can, for example, be in substantially the center of the of the lower bone contact member 450, enabling the lower bone contact member to angulate in either the anterior or posterior direction.

In still another aspect, the VBR device comprises an inner and outer sleeve 500, 550, wherein the outer and inner sleeves are configured to move longitudinally with respect to one another from the retracted position to the expanded position. The inner and outer sleeve define an interior cavity 555. In an exemplified aspect, an interior surface 560 of the outer sleeve 550 comprises a toothed surface 565. In one aspect, the exterior surface 510 of the inner sleeve 500 comprises a toothed surface 515, as well. Each tooth can comprise a cam surface 516, 566 and a flat surface 517, 567. In one aspect, the toothed surfaces are complimentarily opposite, meaning that in the expanding direction, the cam surface of a tooth on the outer sleeve mates with the cam surface of a tooth on the inner sleeve and, in the retracting direction, the flat surface of a tooth on the outer sleeve engages the flat surface of a tooth on the inner sleeve This relationship permits the two sleeves to move in the expanding direction in a ratcheting manner, but prevents the two sleeves to move in the retracting direction. As one skilled in the art can appreciate, in lieu of complimentary toothed surfaces, the inner and outer sleeves can comprise one toothed surface and define a complimentary recess 520 on the other surface, where the recess 520 has a flat interior edge 522 that compliments the flat surface 567 of the tooth of the other surface.

In this aspect, the upper bone contact member can be hingedly attached to a top portion 580 of the outer sleeve and the lower bone contact member can be hingedly attached to a lower portion 530 of the inner sleeve. This configuration permits angulation of the bone contact members to compliment the adjacent vertebral bodies. In an exemplified aspect, the inner and outer sleeves nest within one another and define a pillar window 570. In this aspect, the VBR device comprise a pillar 20 configured to fit within the interior cavity 555 to be placed into the interior cavity via the pillar window 570. In an exemplified aspect, a top portion 21 of the pillar is angled and the bottom portion of the pillar 22 is also angled. The top portion 21 of the pillar engages a portion of the upper bone contact member 400 and the angle of the top portion of the pillar places the upper bone contact member to the desired angle for lordosis. Similarly, the bottom portion 22 of the pillar engages a portion of the lower bone contact member 450 and the angle of the lower portion of pillar places the lower bone contact member to the desired angle for lordosis. The pillar, of course, substantially prevents the VBR device from moving from the expanded position to the retracted position.

Figure 42:
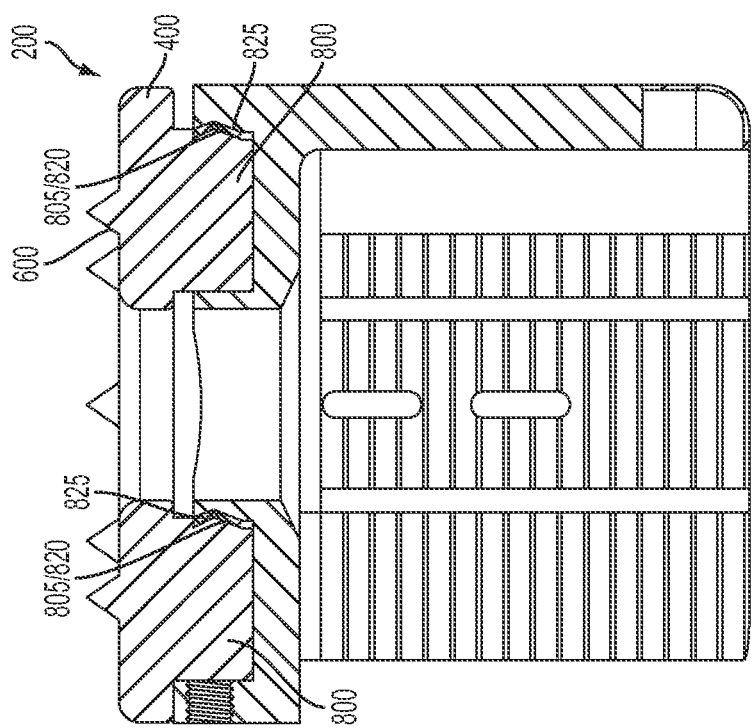
FIG. 42 is a cut-away side view of the outer housing of FIG. 39, cut along line 42-42 of FIG. 40.
Figure 45:
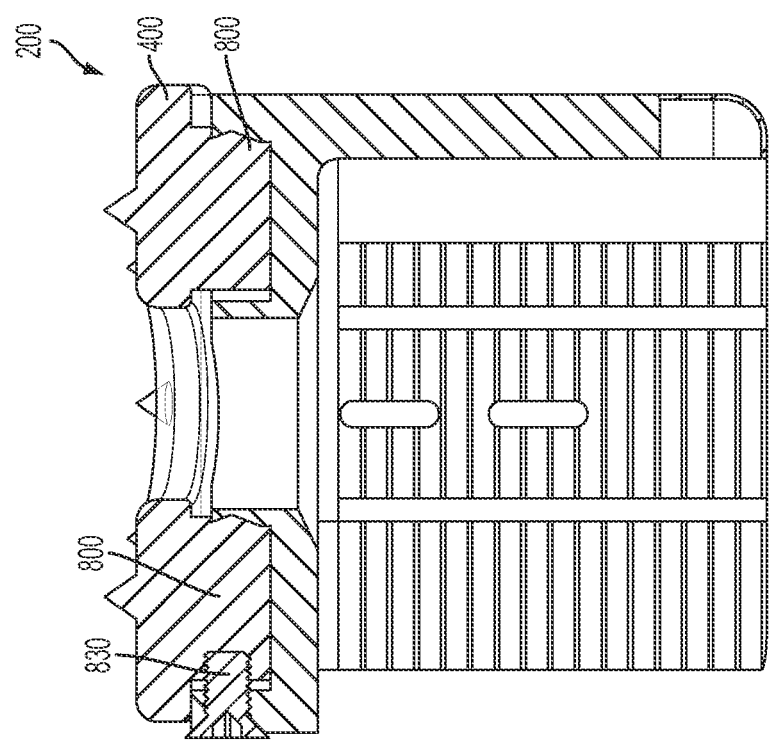
FIG. 45 is a cut-away side view of the outer housing of FIG. 39, cut along line 45-45 of FIG. 43.
Figure 44:
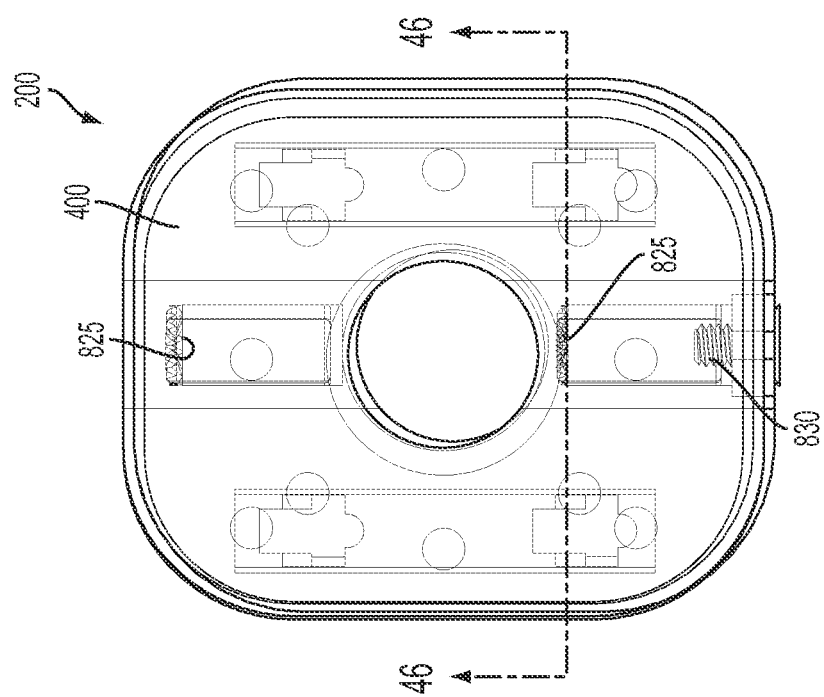
FIG. 44 is a partially transparent top plan view of the outer housing of FIG. 39, showing a trough for receipt of a pivot member.
Figure 46:
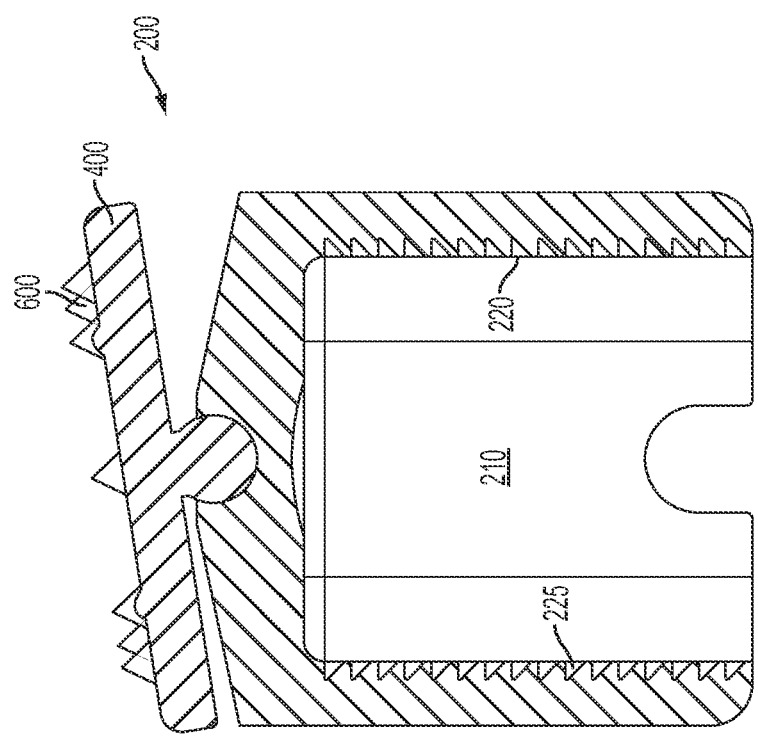
FIG. 46 is a cut-away front view of the outer housing of FIG. 39, cut along line 46-46 of FIG. 44.
Figure 48:
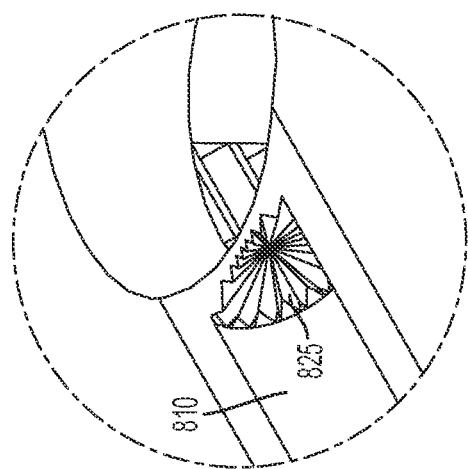
FIG. 48 is a section view of a section of the outer housing of FIG. 39 showing the section of FIG. 47.
Figure 47:
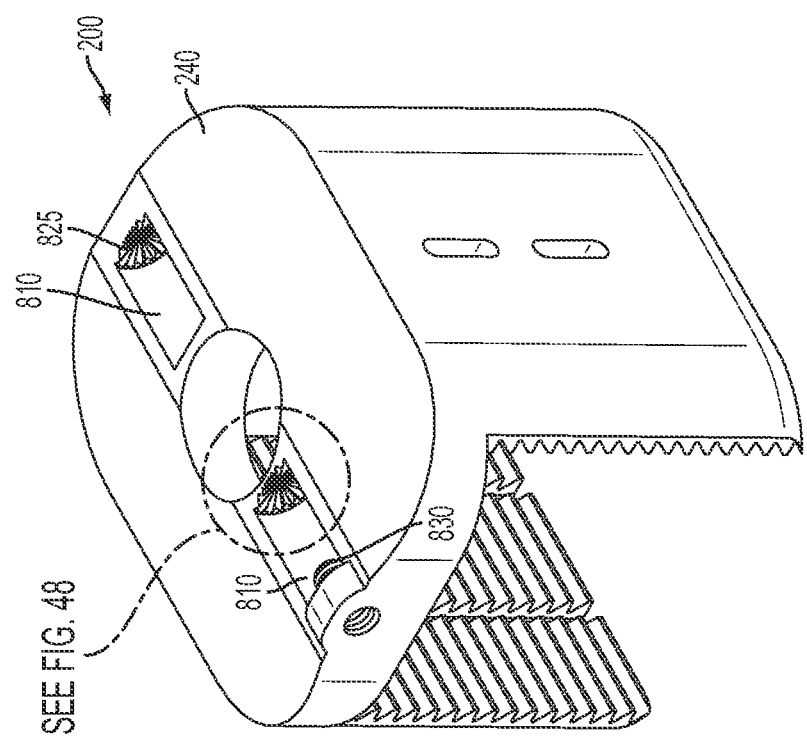
FIG. 47 is a perspective view of the outer housing of FIG. 39, illustrating the trough and engagement portion of the trough.
Figure 49:
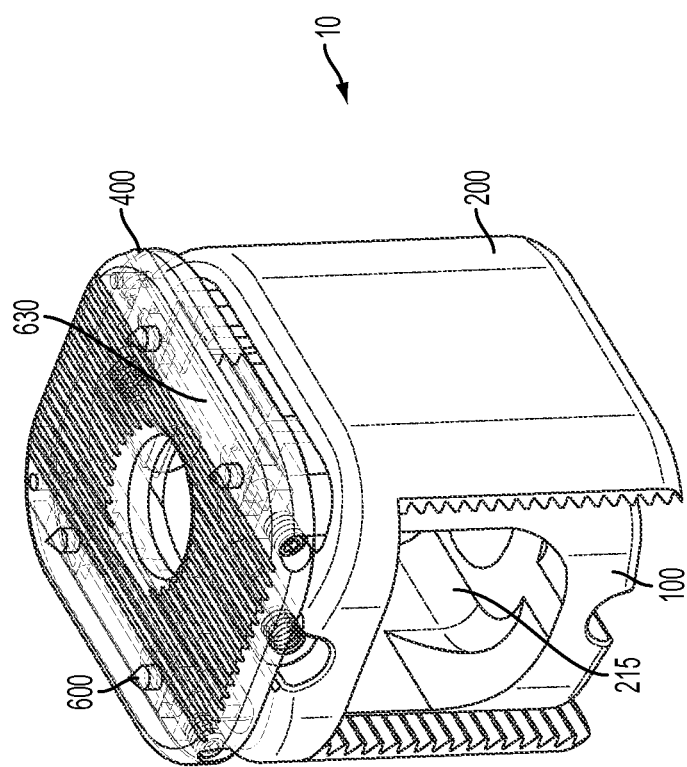
FIG. 49 is a partially transparent perspective view of a VBR device, illustrating deployable spikes corresponding to an upper bone contact member.
Figure 50:
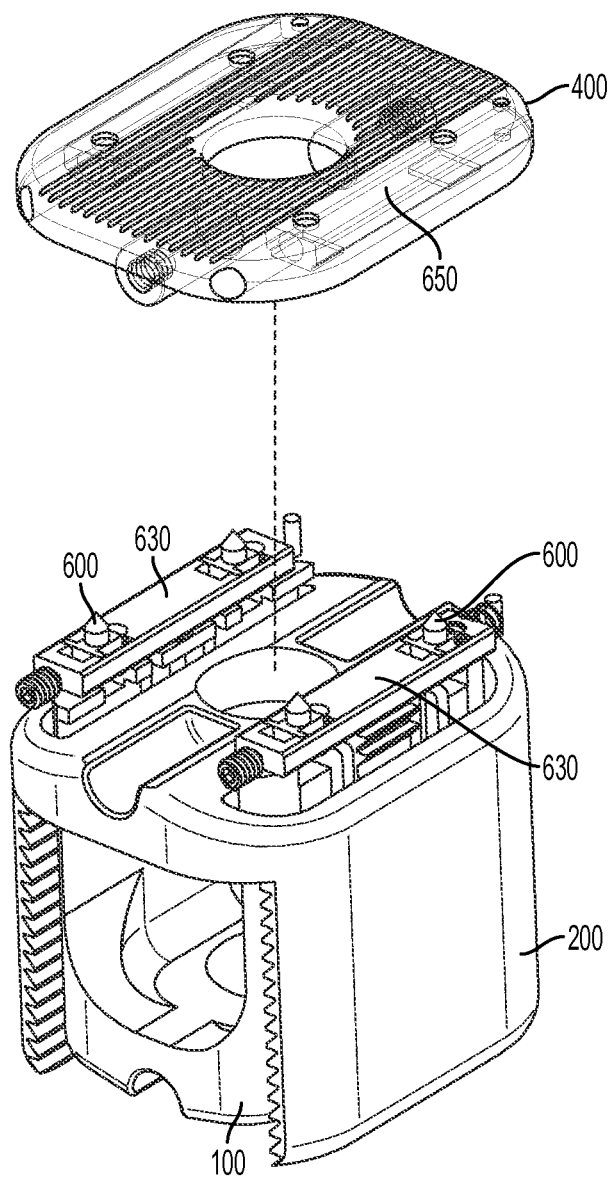
FIG. 50 is a partially transparent cut-away perspective view of the VBR device of FIG. 49, illustrating ramp members associated with deployable spikes.
Figure 50A:
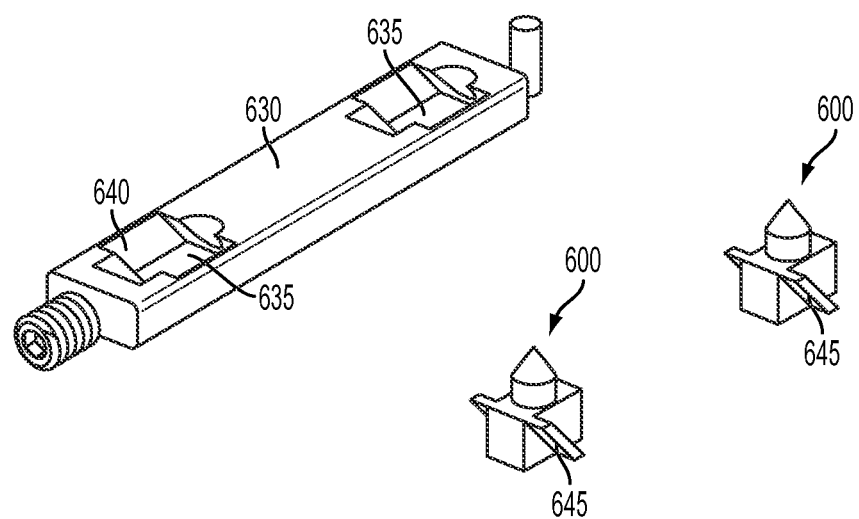
FIG. 50A is a perspective view of a ramp member and deployable spikes for use in the VBR device of FIG. 49.
Figure 52:
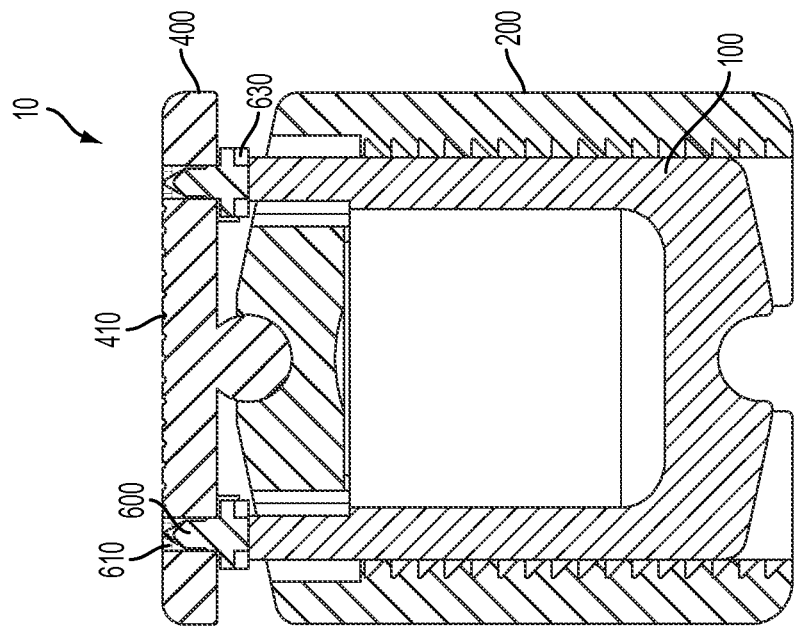
FIG. 52 is a cut-away front view of the VBR device of FIG. 49, cut along line 52-52 of FIG. 51.
Figure 51:
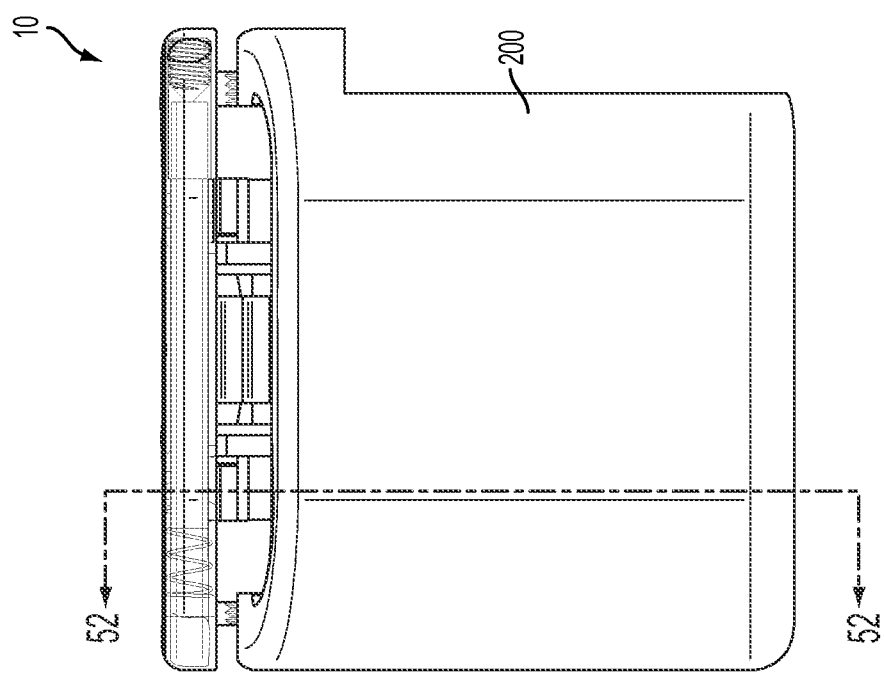
FIG. 51 is a side view of the VBR device of FIG. 49, illustrating the spikes in a retracted position.
Figure 54:
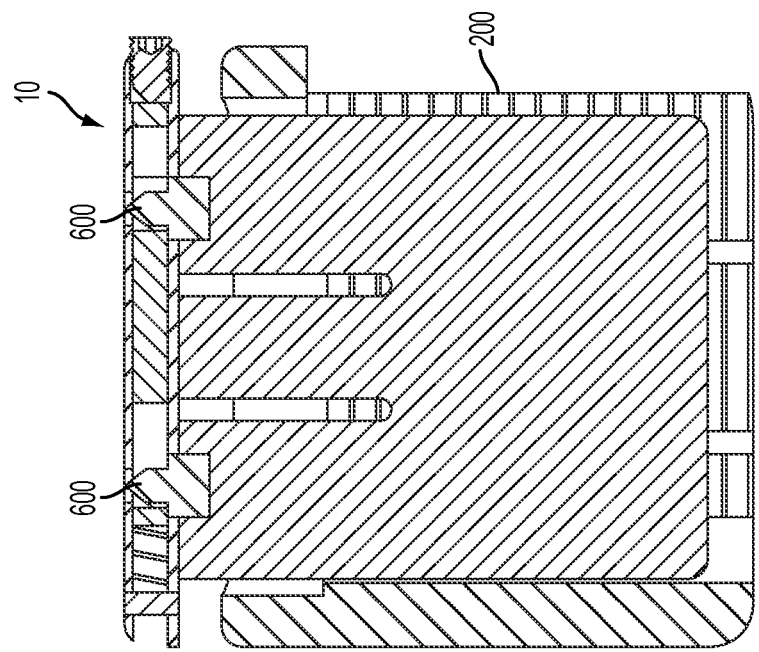
FIG. 54 is a cut-away side view of the VBR device of FIG. 49, cut along line 54-54 of FIG. 53.
Figure 53:
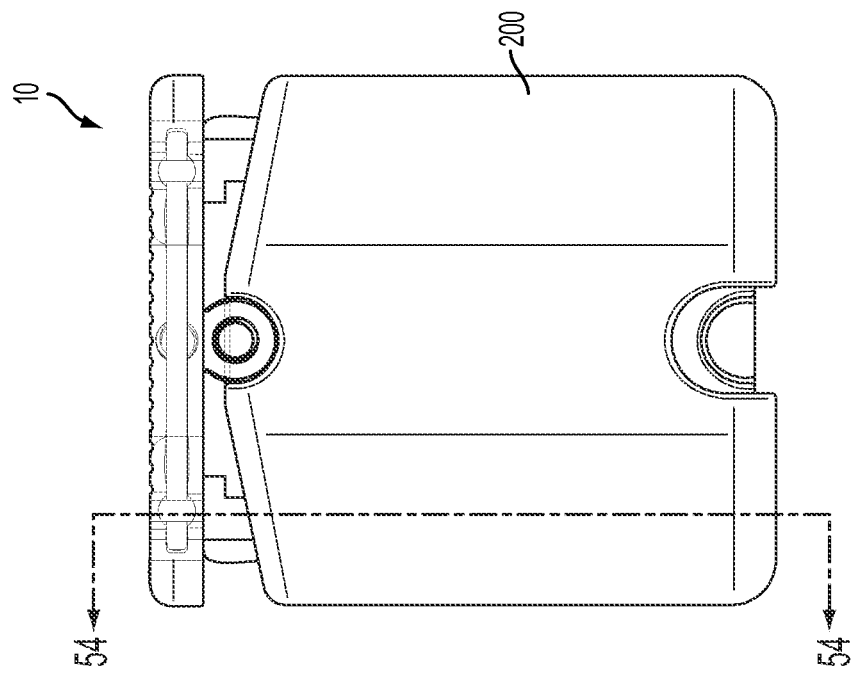
FIG. 53 is a rear view of the VBR device of FIG. 49, illustrating the spikes in a retracted position.
Figure 56:
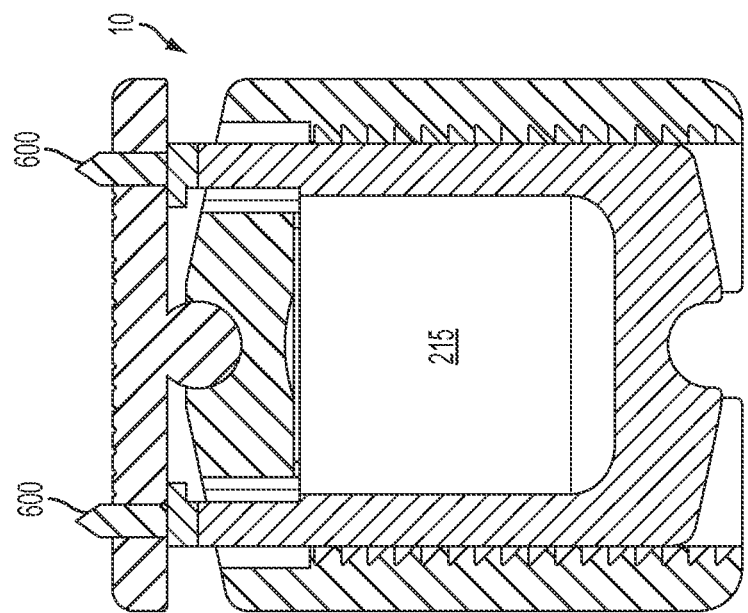
FIG. 56 is a cut-away front view of the VBR device of FIG. 49, cut along line 56-56 of FIG. 55.
Figure 55:
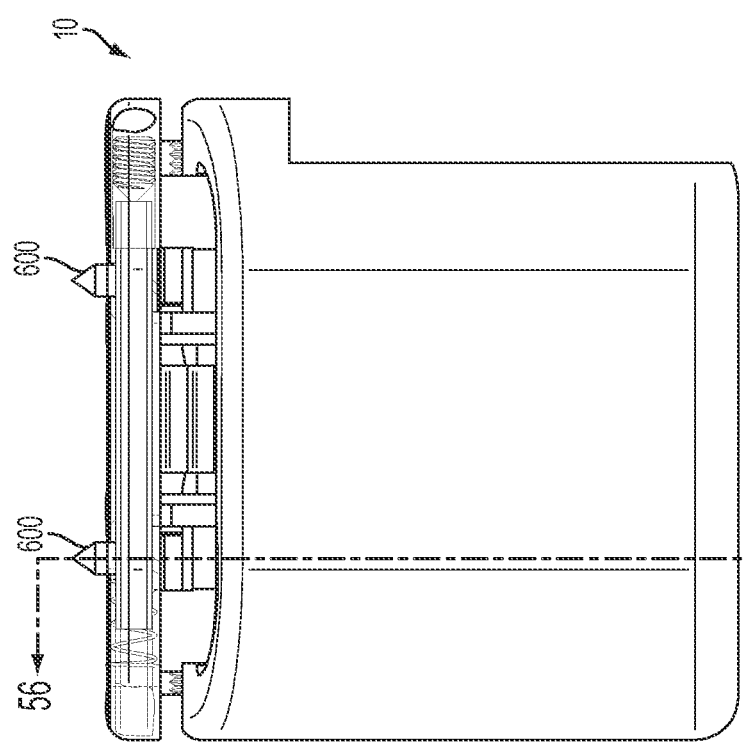
FIG. 55 is a side view of the VBR device of FIG. 49, illustrating the spikes in a deployed position.
Figure 58:
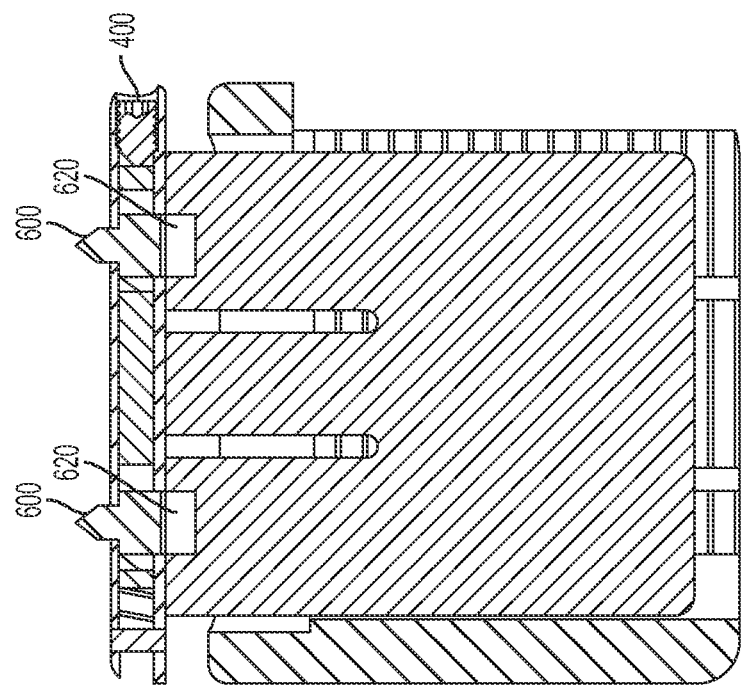
FIG. 58 is cut-away side view of the VBR device of FIG. 49, cut along line 58-58 of FIG. 57.
Figure 57:
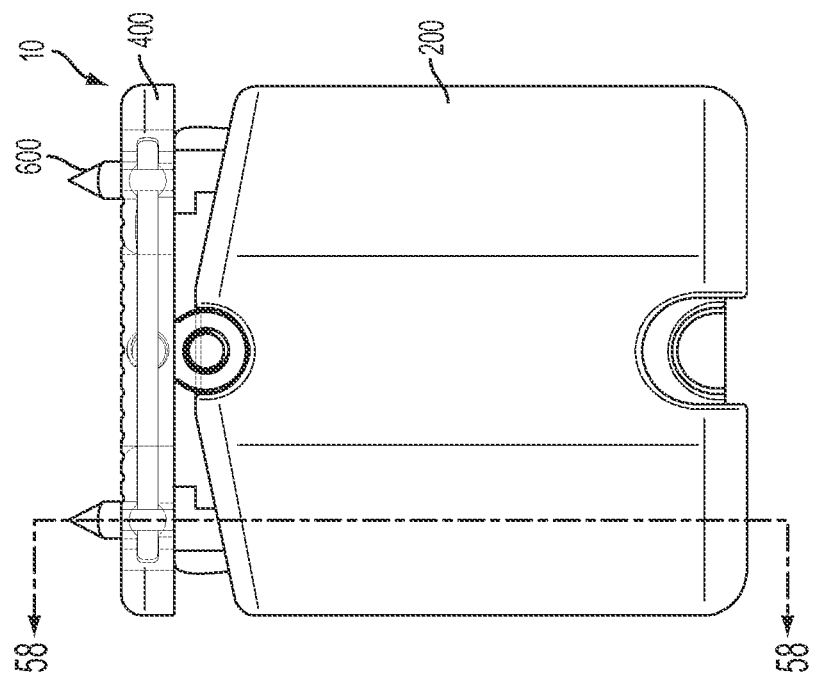
FIG. 57 is a rear view of the VBR device of FIG. 49, illustrating the spikes in a deployed position.
Figure 60:
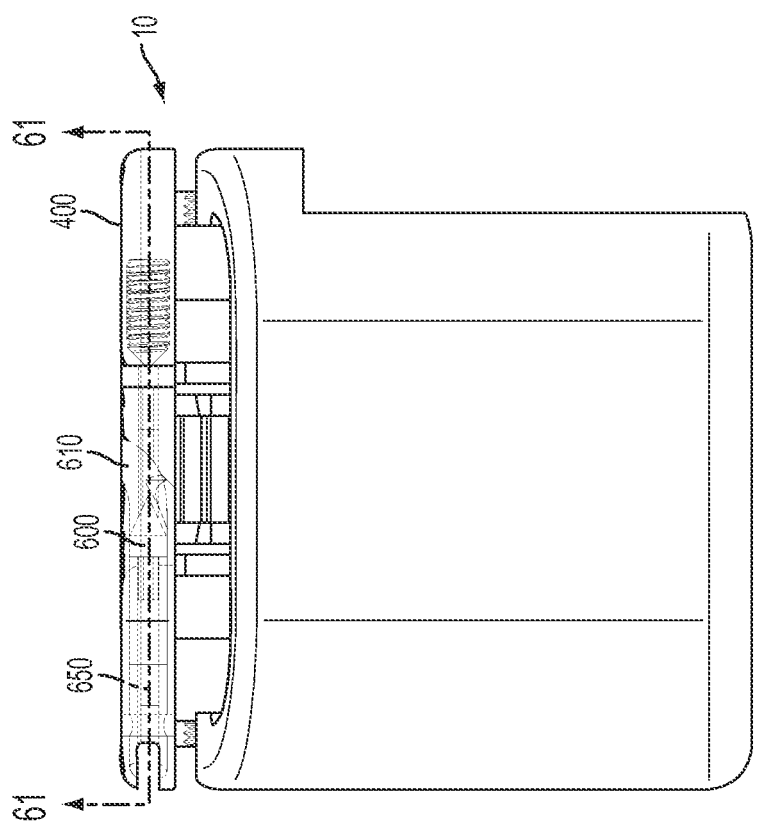
FIG. 60 is a partially transparent side view of the VBR device of FIG. 59, illustrating the spikes in a retracted position.
Figure 59:
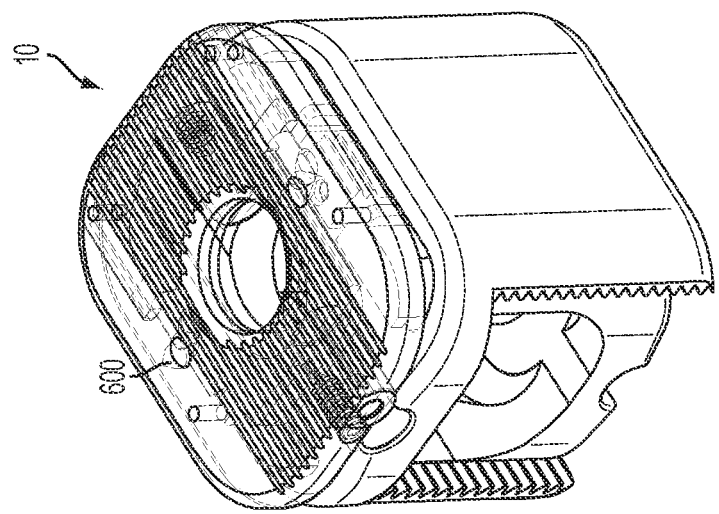
FIG. 59 is a partially transparent perspective view of a VBR device illustrating deployable flexible spikes.
Figure 62:
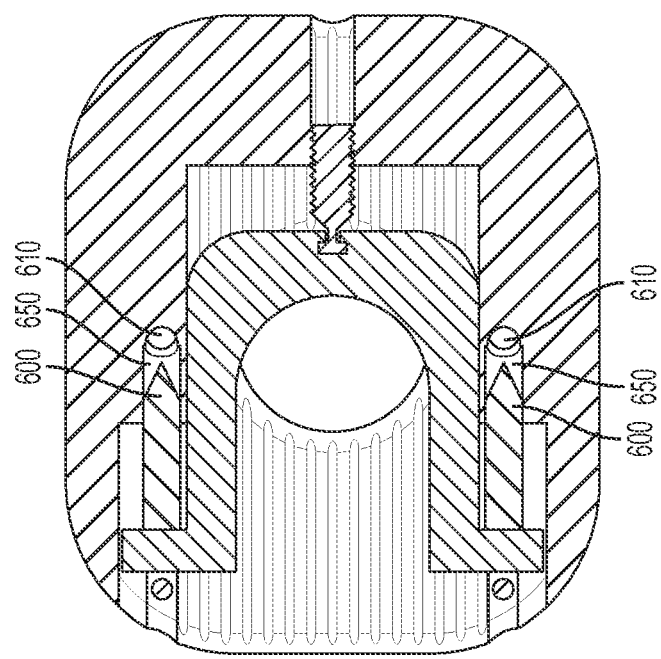
FIG. 62 is a rear view of the VBR device of FIG. 59, illustrating the spikes in a retracted position.
Figure 61:
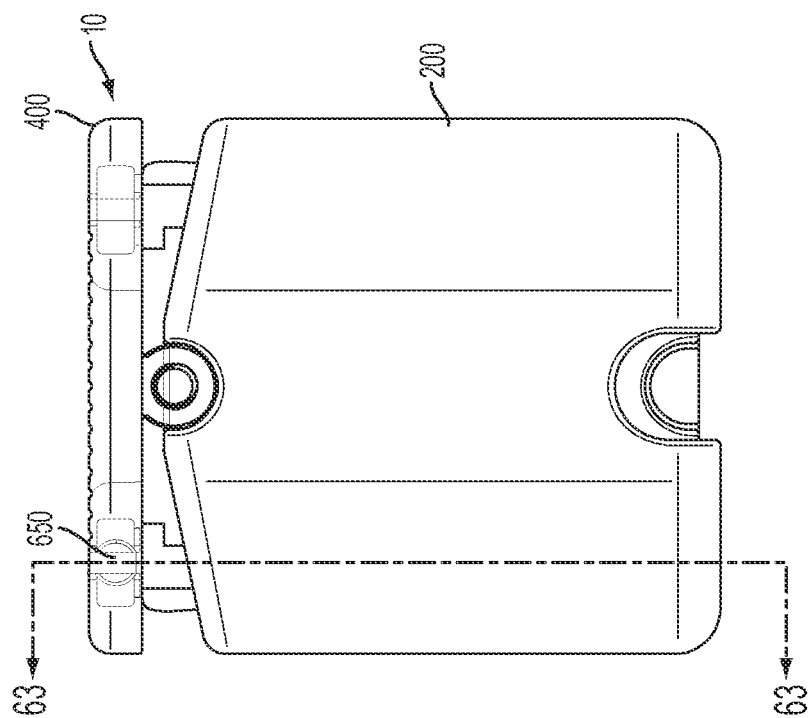
FIG. 61 is a cut-away top plan view of the VBR device of FIG. 59, cut along line 61-61 of FIG. 60.
Figure 64:
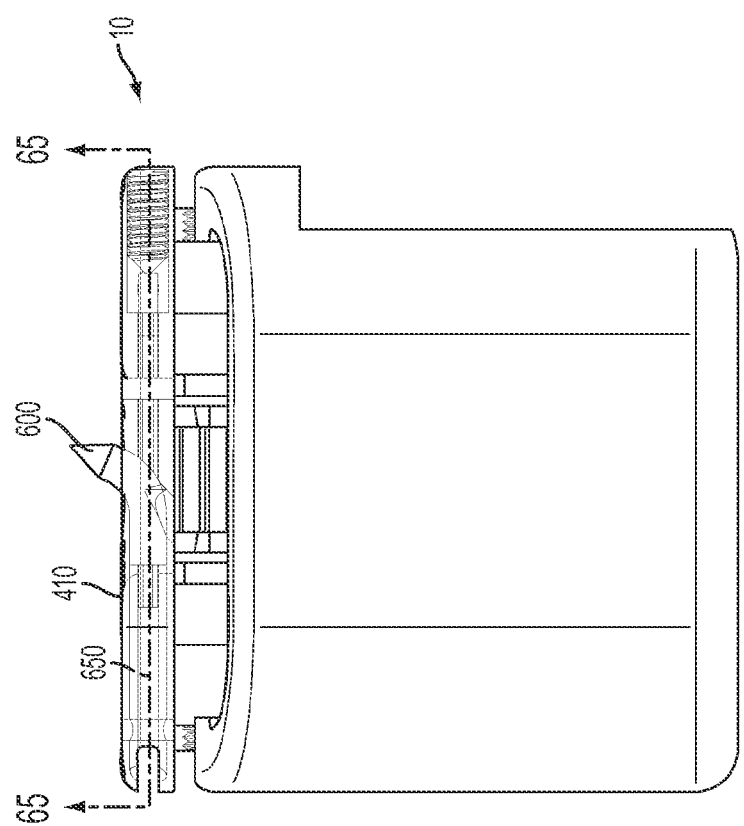
FIG. 64 is a partially transparent side view of the VBR device of FIG. 59, illustrating the spikes in a deployed position.
Figure 63:
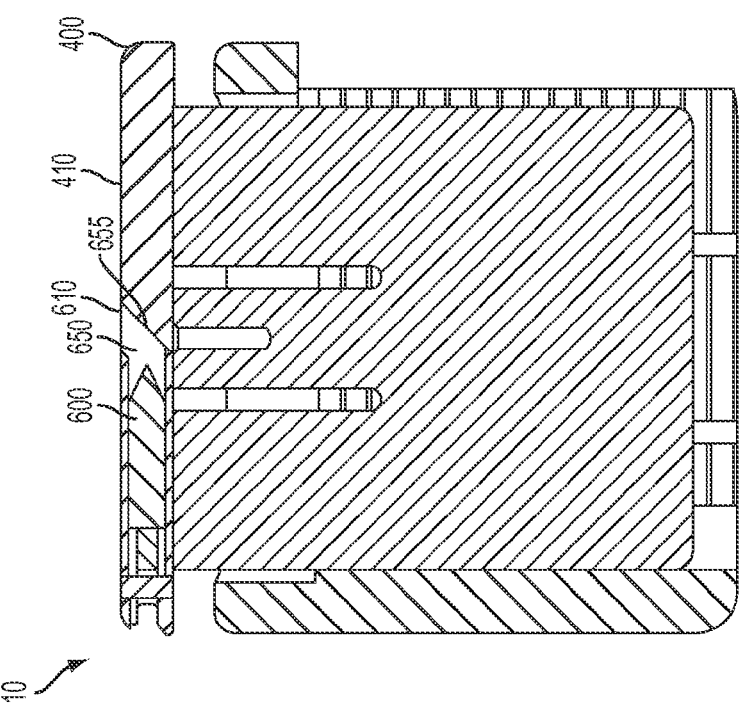
FIG. 63 is a cut-away side view of the VBR device of FIG. 59, cut along line 63-63 of FIG. 62.
Figure 66:
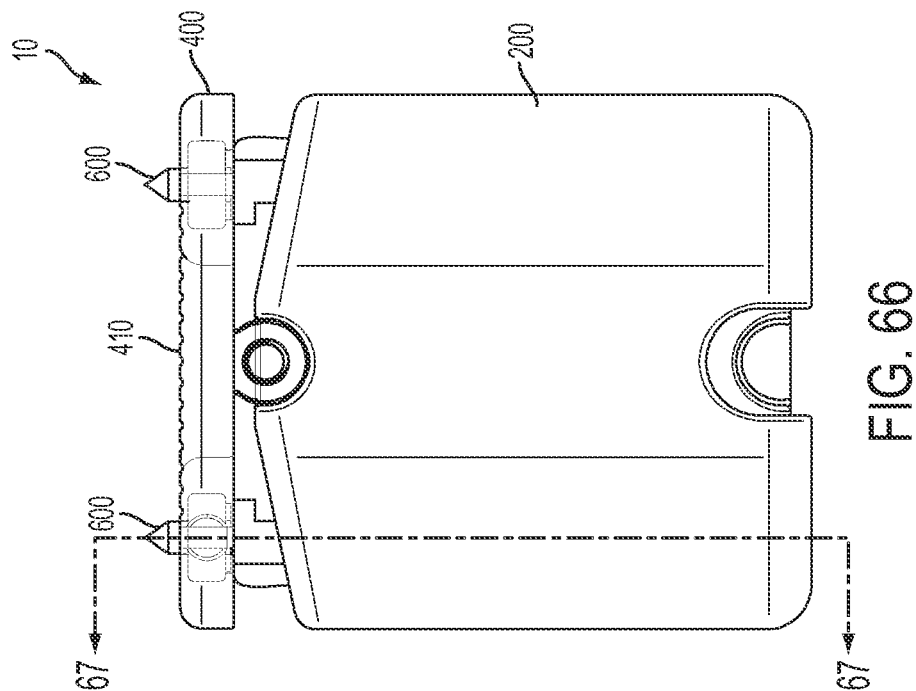
FIG. 66 is a rear view of the VBR device of FIG. 59, illustrating the spikes in a deployed position.
Figure 65:
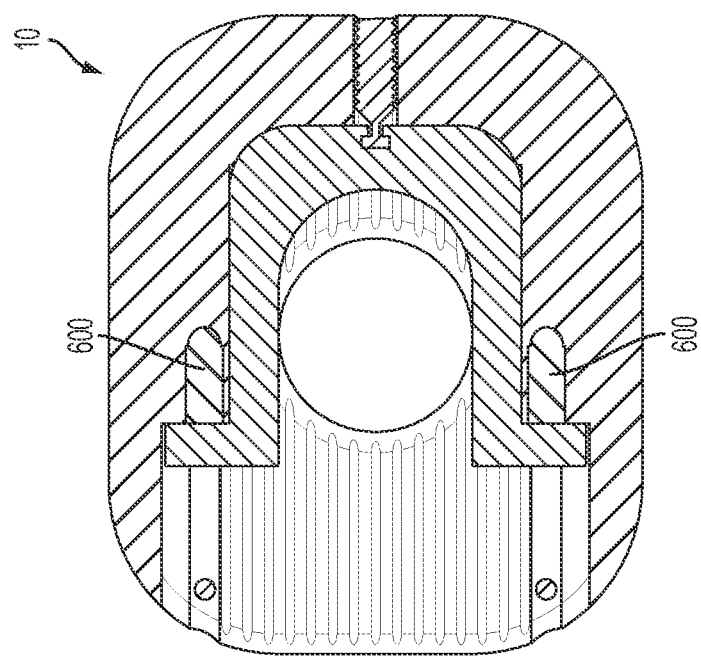
FIG. 65 is a cut-away top plan view of the VBR device of FIG. 59, cut along line 65-65 of FIG. 64.
Figure 68:
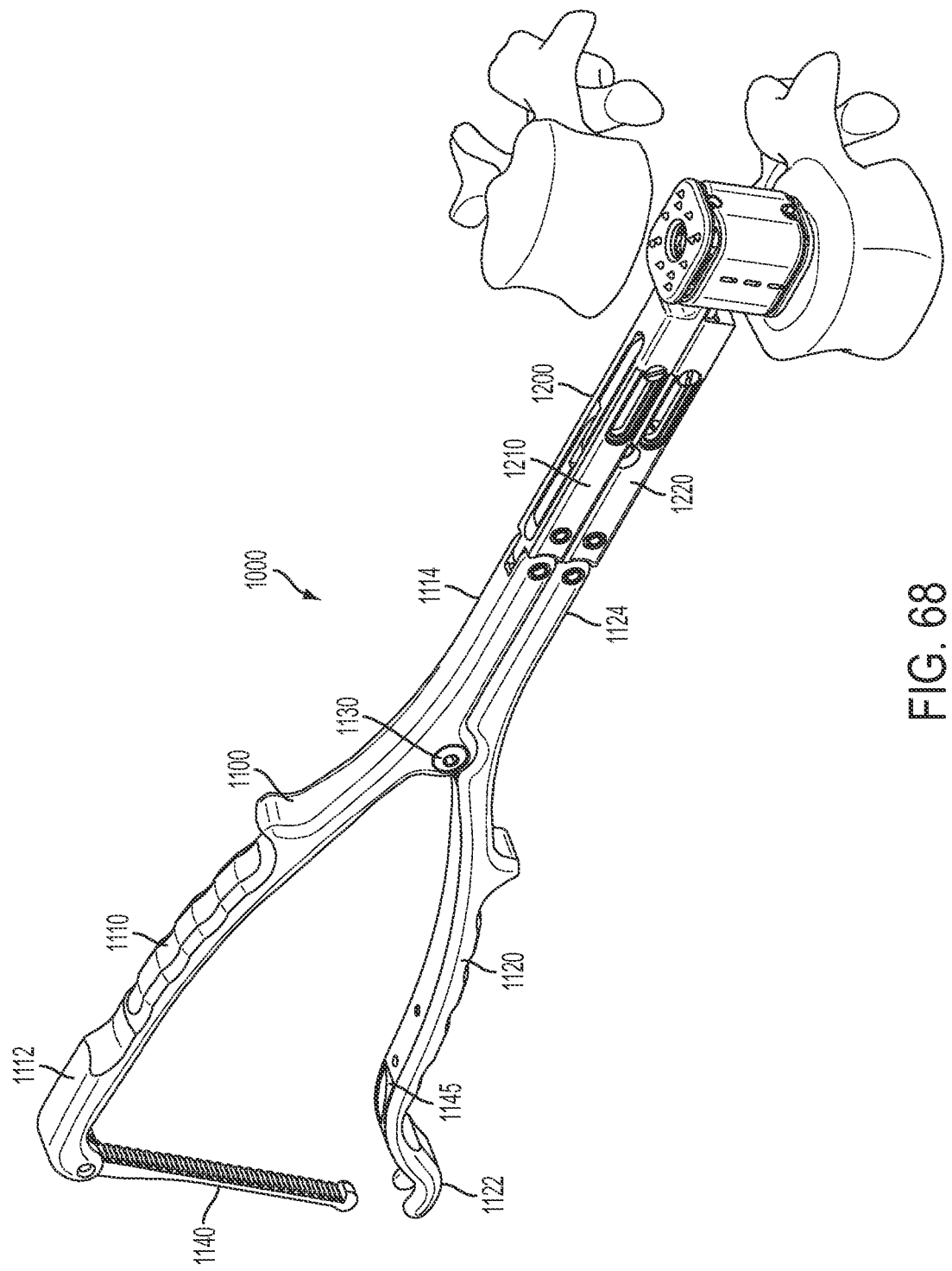
FIG. 68 is a perspective view of one aspect of a VBR device and a VBR device expansion tool.

One or both of the upper and lower bone contact members 400, 450 can comprise spikes 600 or protrusions to facilitate engagement with the respective vertebral bone. The spikes can be integral with the respective upper or lower bone contact member or they can be deployed after insertion into the disc space. In one exemplified aspect, as illustrated in FIG. 42, the respective bone contact member can define at least one spike aperture 610 in communication with a spike cavity 620. A spike can be sized to fit substantially completely therein the spike cavity 620. In one aspect, a ramp member 630 can be positioned within a channel 650 defined in the bone contact member defining an orifice 635 that is partially coaxial with the spike cavity 620. The edges of the orifice and the spike comprise complimentary cam 640 and follower 645 surfaces such that, when the ramp member 630 is moved in a first direction, the spike rides along the ramp member, raising it to extend the distal portion of the spike above the bone contact surface of the bone contact member. Of course, it is contemplated that the spike can comprise a plurality of spikes and the spike cavity can comprise a plurality of spike cavities. Additionally, the ramp member can comprise a plurality of ramp members. Each ramp member may define a plurality of orifices, each corresponding to a spike and spike cavity, as illustrated in FIG. 42.

In another aspect, the spikes 600 can comprise a flexible material, such as Nitinol or spring steel. In this aspect, the spikes can be initially embedded within a channel 650 in the respective bone contact member in a plane that is substantially parallel to the respective bone contact surface. Each of the spike apertures 610 can be associated with a ramped or angled portion 655 of the bone contact member such that, when the flexible spike is moved toward the spike aperture, the spike will angle upward and through the spike aperture.

Figure 25:
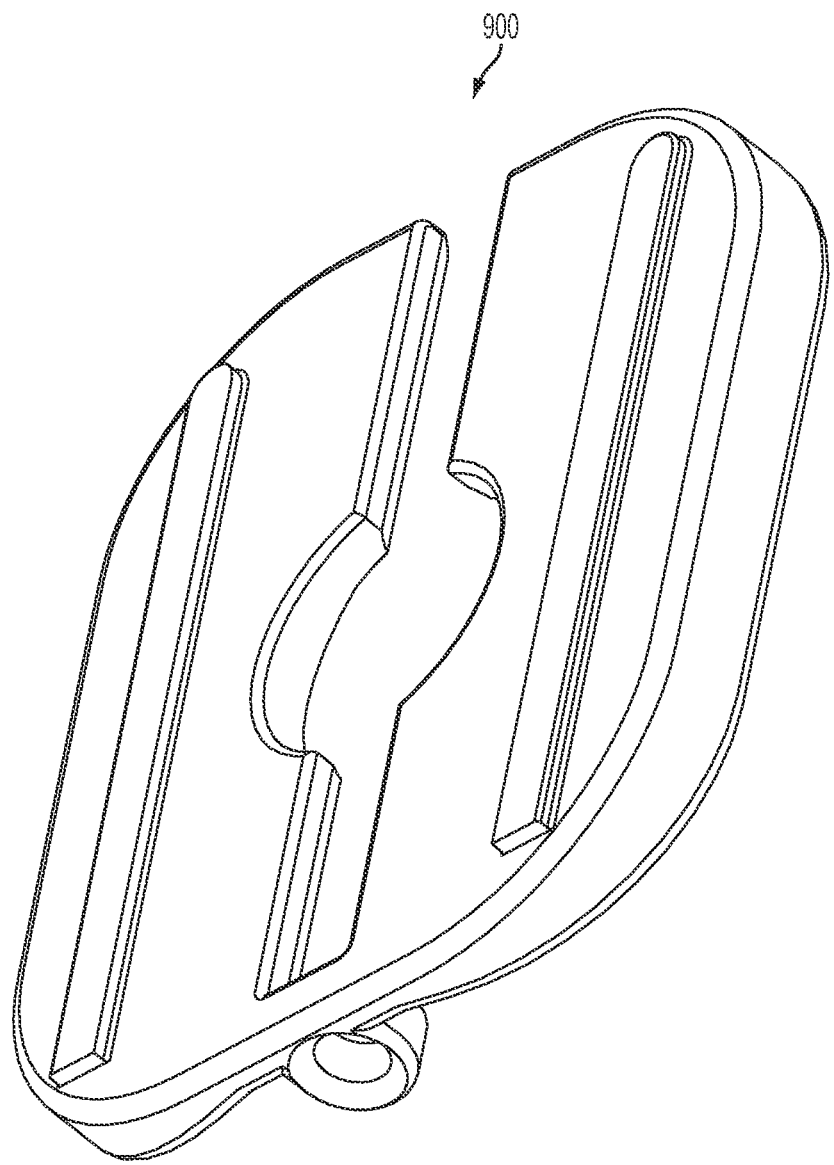
FIG. 25 is a perspective view of a wedge member for use in a VBR device.
Figure 26:
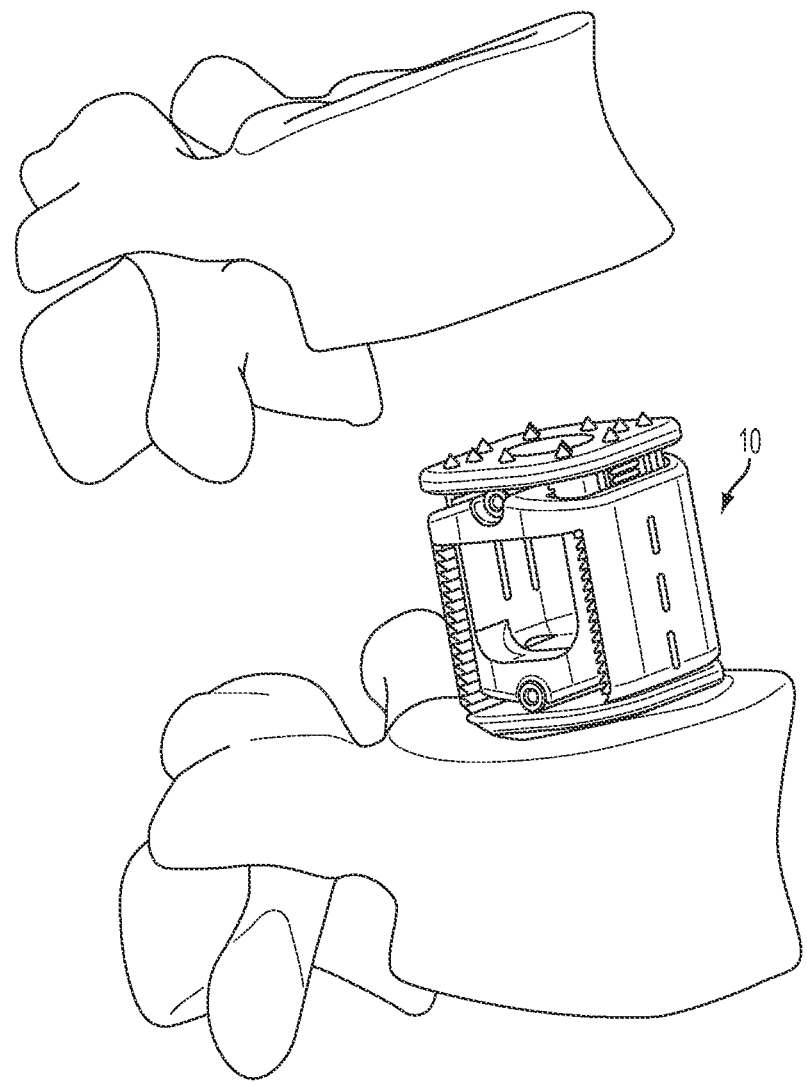
FIG. 26 is a perspective view of the VBR device of FIG. 19 in the unexpanded position, illustrating the VBR device between two vertebrae.
Figure 27:
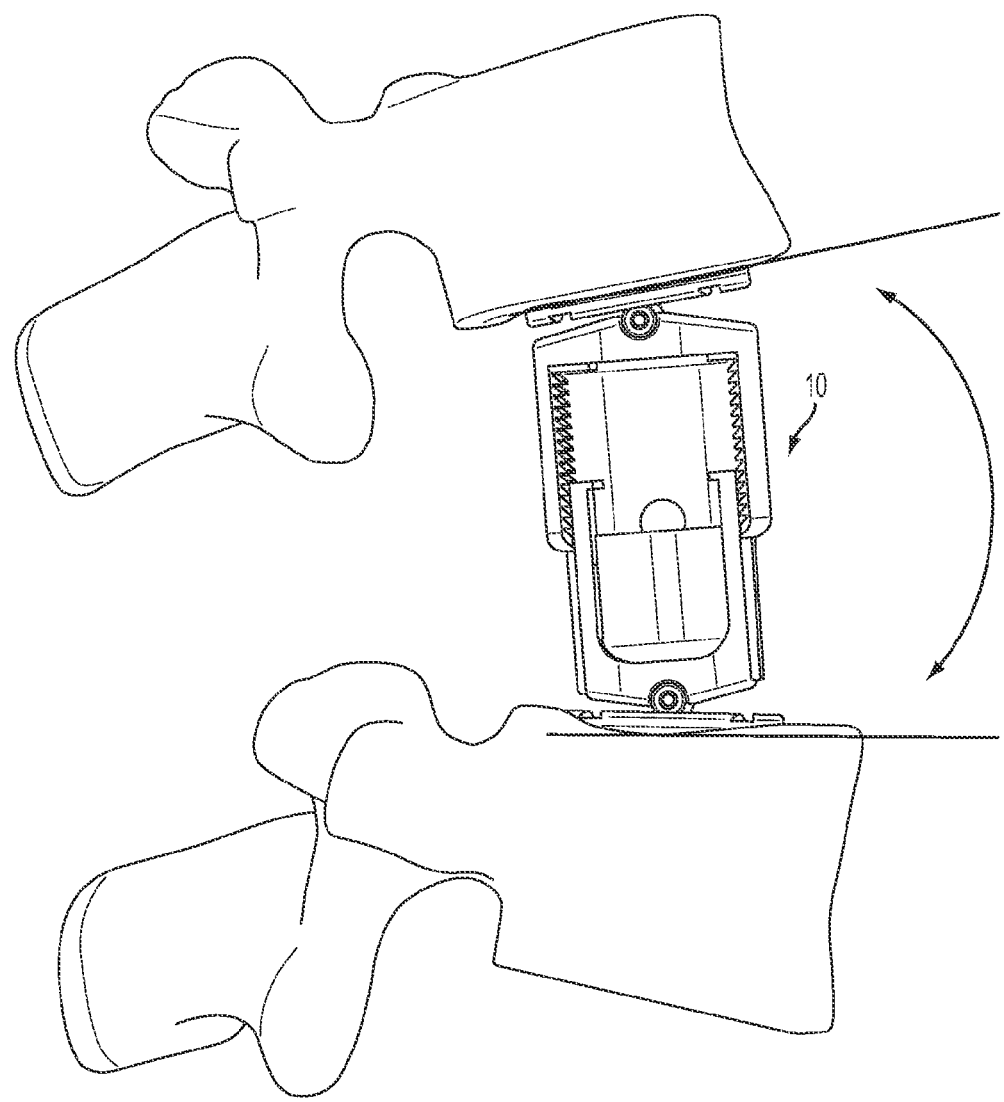
FIG. 27 is a front view of the VBR device of FIG. 19 in the expanded position, illustrating the VBR device between two vertebrae.
Figure 28:
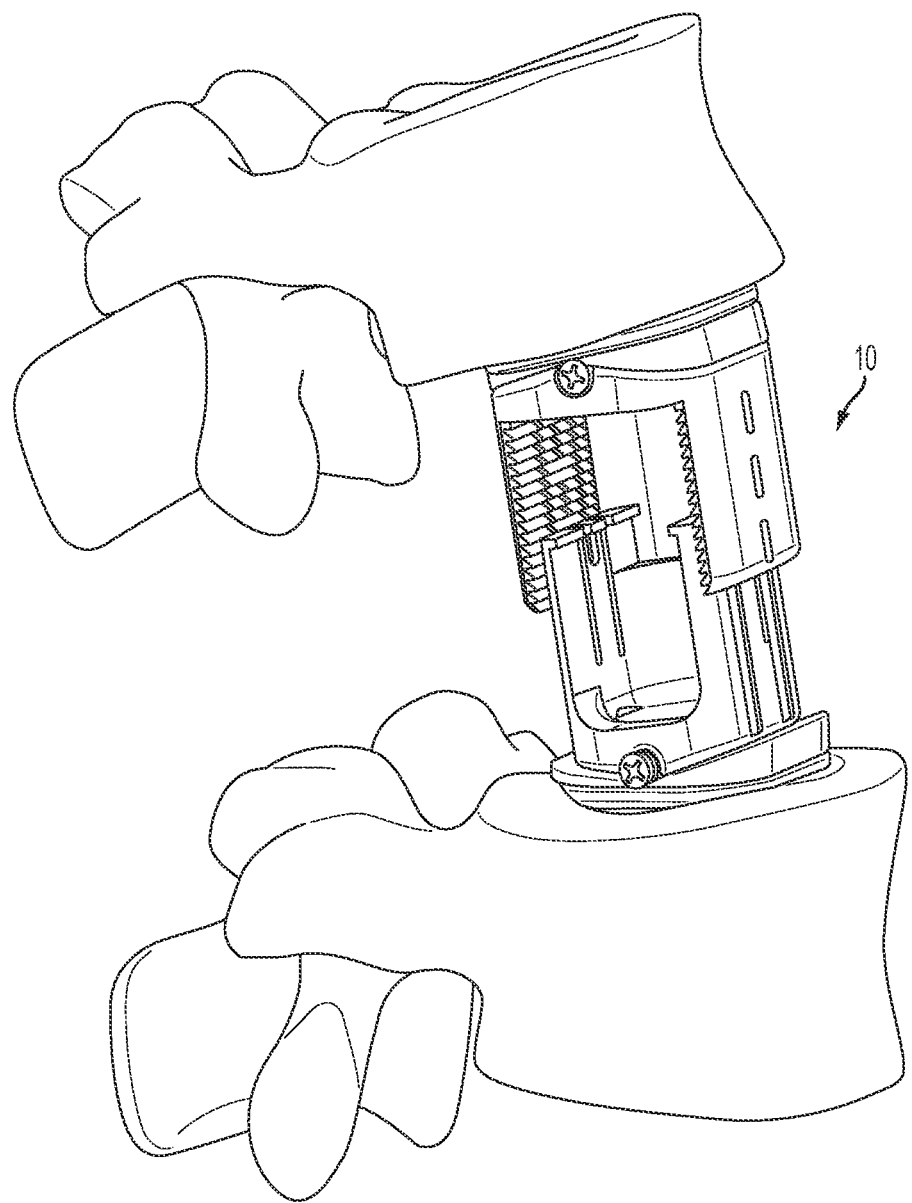
FIG. 28 is a perspective view of the VBR device of FIG. 19 in the expanded position, illustrating the VBR device between two vertebrae.
Figure 29:
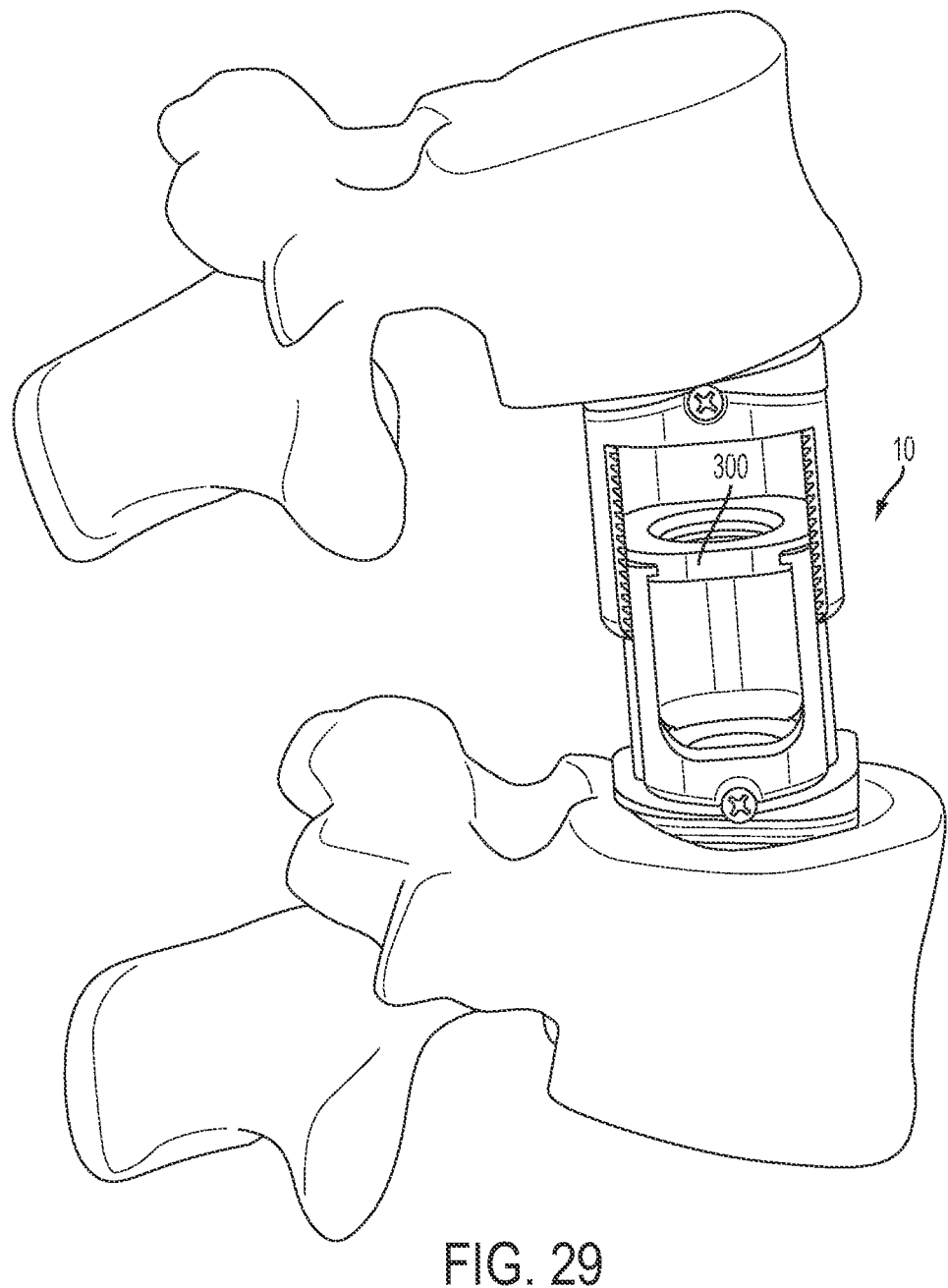
FIG. 29 is a perspective view of the VBR device of FIG. 19 in the expanded position, illustrating the VBR device between two vertebrae with a retention member in place.
Figure 30:
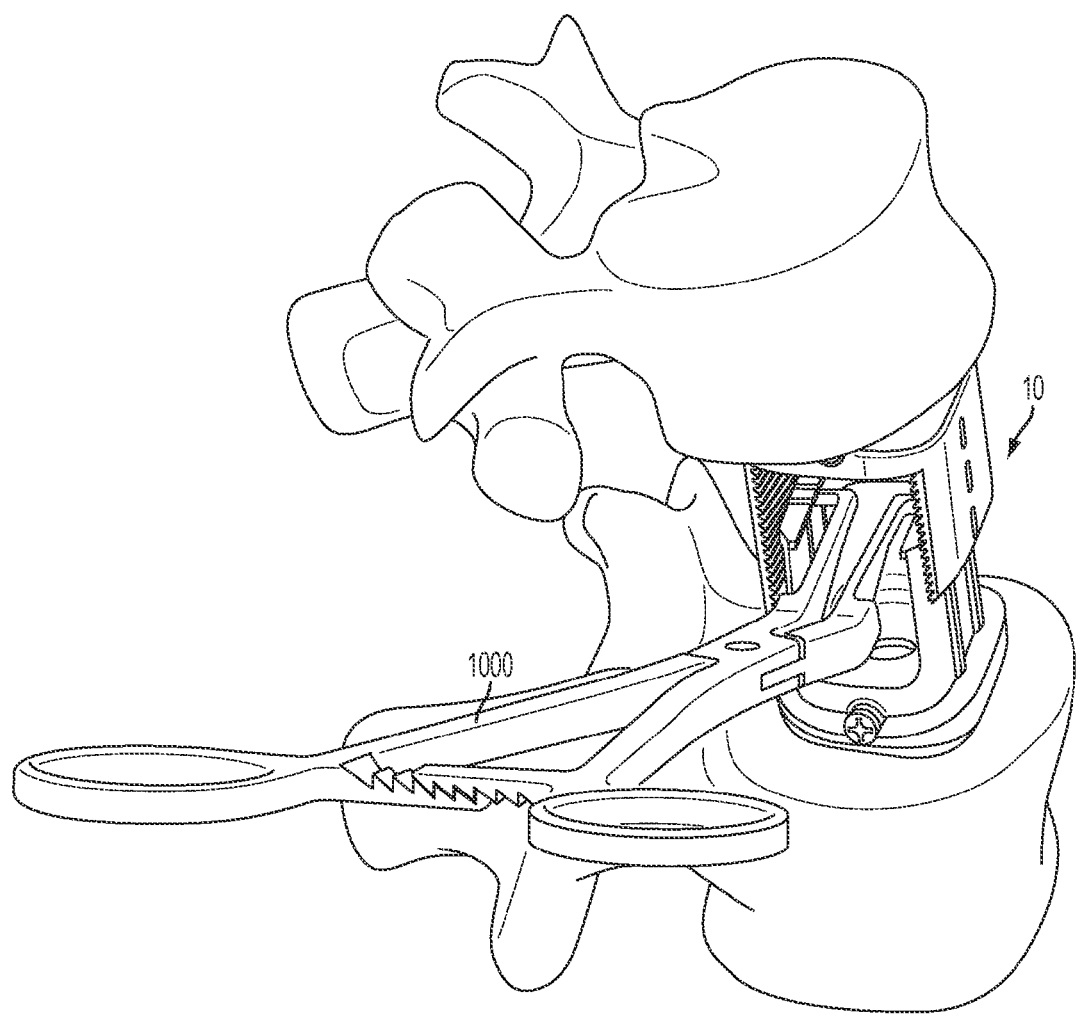
FIG. 30 is a perspective view of the VBR device of FIG. 19, showing the VBR device being expanded by an expansion tool.

In one exemplified aspect, one or both of the bone contact members can be locked in angular position, substantially restraining the respective bone contact member from pivoting with respect to the respective inner or outer housing. In one aspect, as shown in FIG. 25, the respective bone contact member can comprise a blade 700 positioned on a second surface 420, 470 of the bone contact member 400, 450, opposite the bone contact surface, and substantially perpendicular thereto the second surface. In this aspect, the top of the outer housing, or the bottom of the inner housing, depending on which bone contact member is being discussed, can define a blade slot 710 configured for receipt of the blade 700. The respective housing can also define a threaded aperture 720 configured for receipt of a set screw 730 adapted to fit within the threaded aperture 720 and engage a portion of the blade 700 to substantially fix its position with respect to the respective housing. As shown in the figures, the blade can define a plurality of blade apertures into which the end of the set screw can engage to assist in holding the respective bone contact member in angular position.

Figure 32:
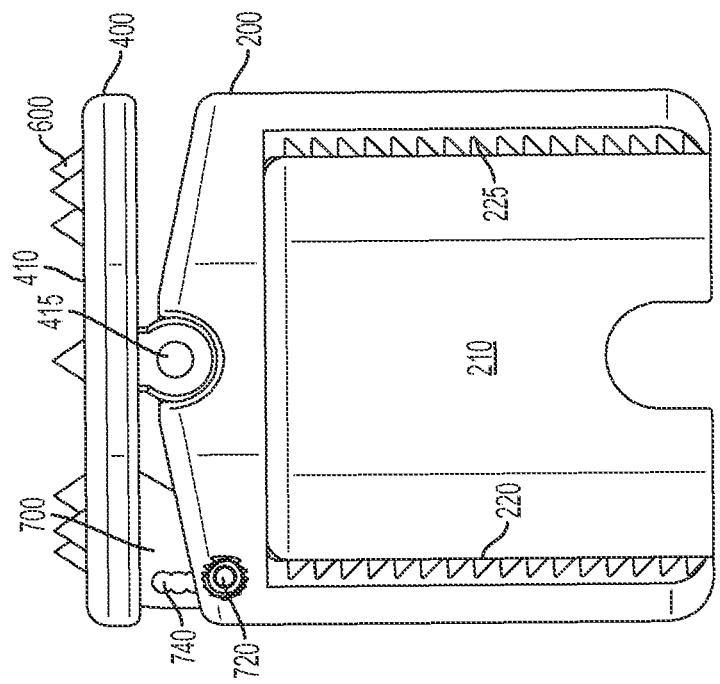
FIG. 32 is a front view of the outer housing of FIG. 31, illustrating a blade and slot for locking the angular position of the bone contact member.
Figure 31:
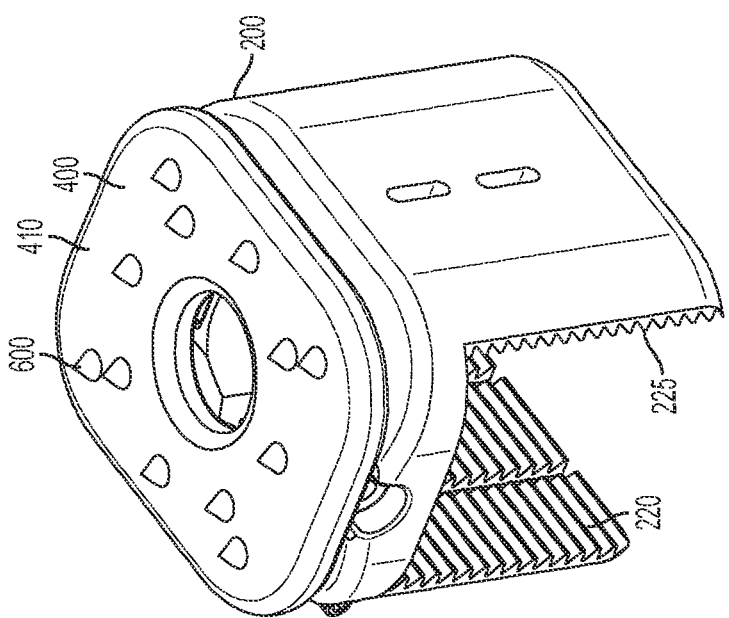
FIG. 31 is a perspective view of an outer housing for a VBR device.
Figure 34:
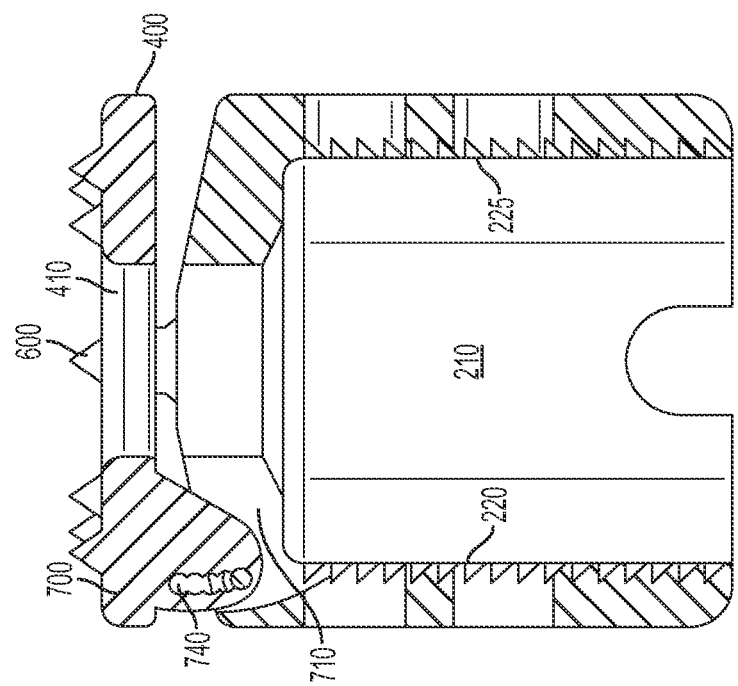
FIG. 34 is a cut-away front view of the outer housing of FIG. 31, cut along line 32-32.
Figure 33:
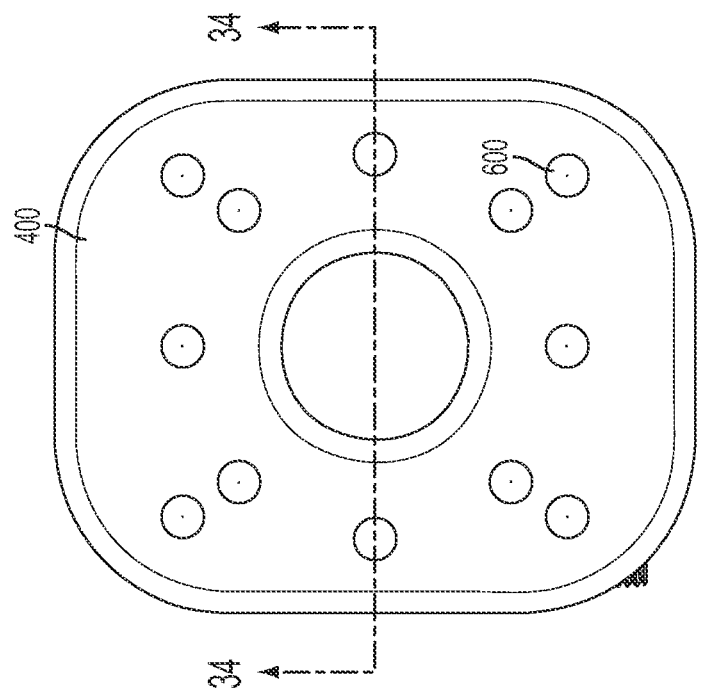
FIG. 33 as a top view of the outer housing of FIG. 31.
Figure 36:
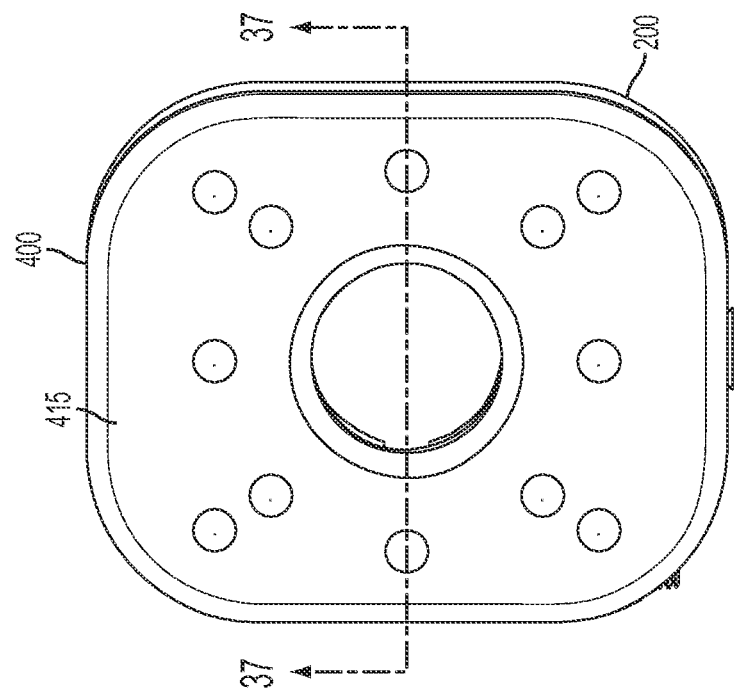
FIG. 36 is a top plan view of the outer housing of FIG. 31.
Figure 35:
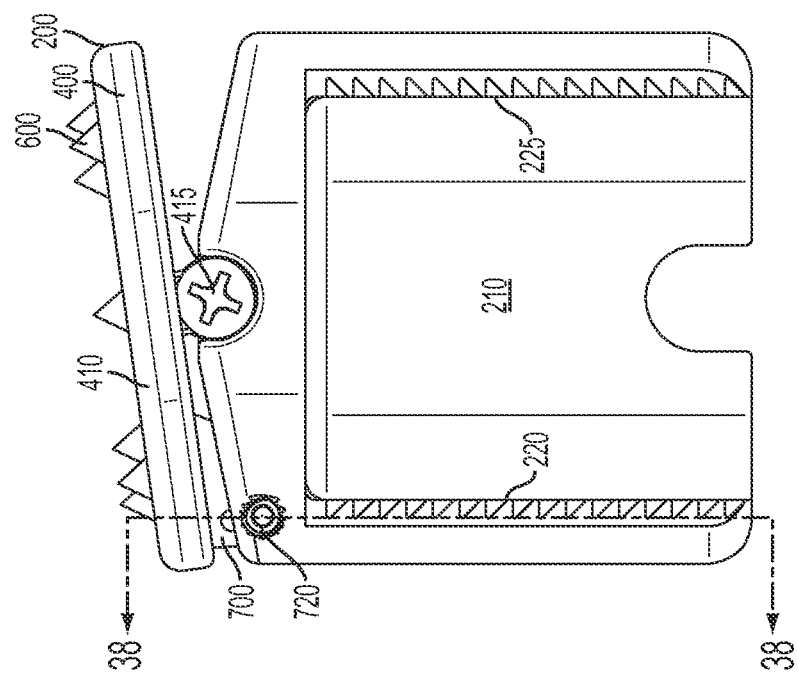
FIG. 35 is a front view of the outer housing of FIG. 31, illustrating a set screw to lock the blade into position.
Figure 39:
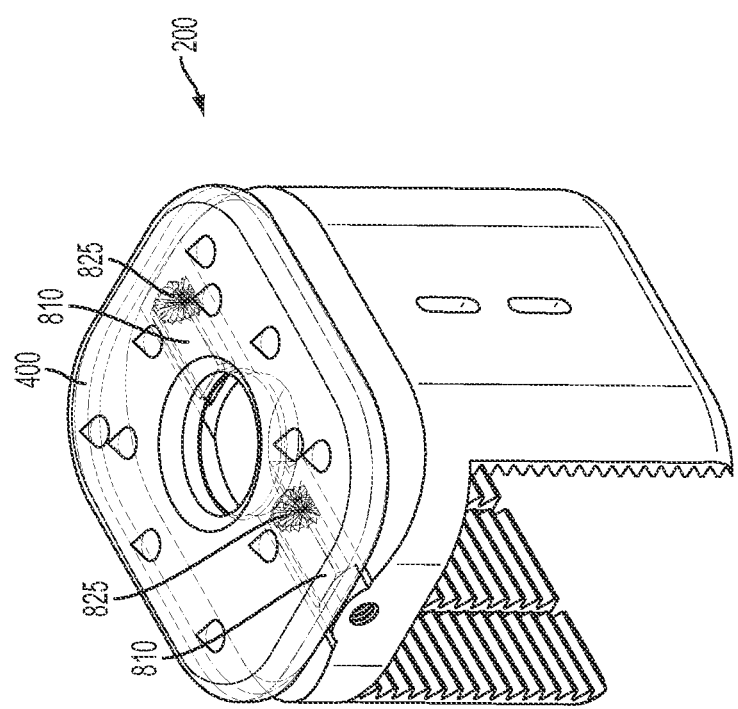
FIG. 39 is a partially transparent perspective view of an outer housing for a VBR device having an elongate pivot member to lock the angular position of the bone contact member.
Figure 41:
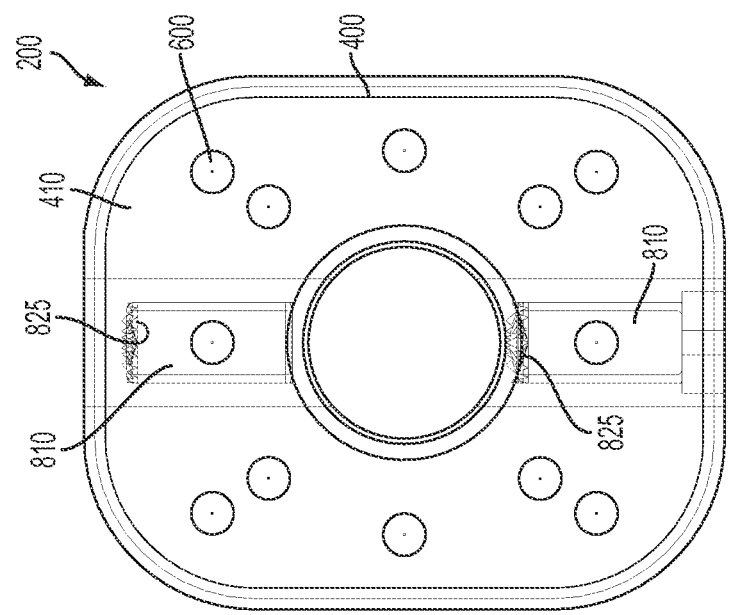
FIG. 41 is a partially transparent top plan view of the outer housing of FIG. 39.
Figure 40:
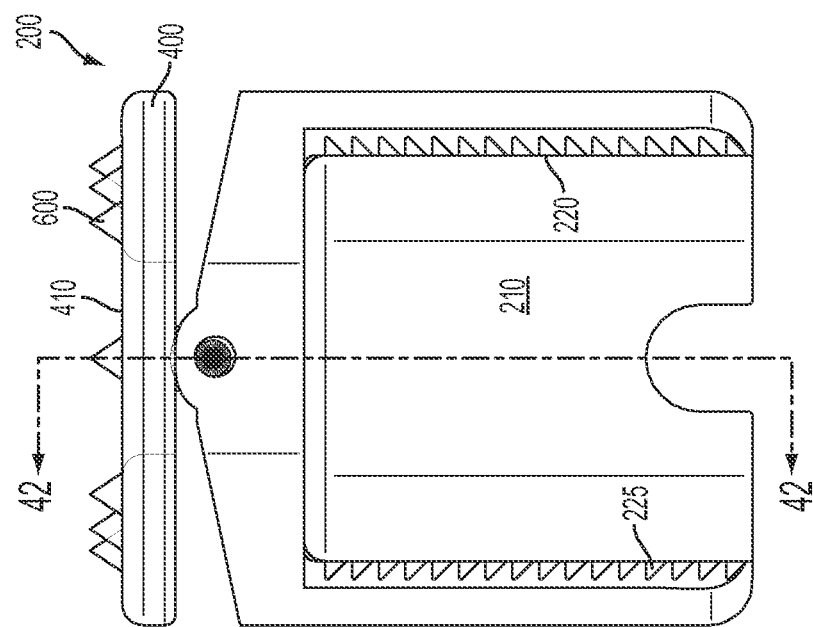
FIG. 40 is a front view of the outer housing of FIG. 39.
Figure 43:
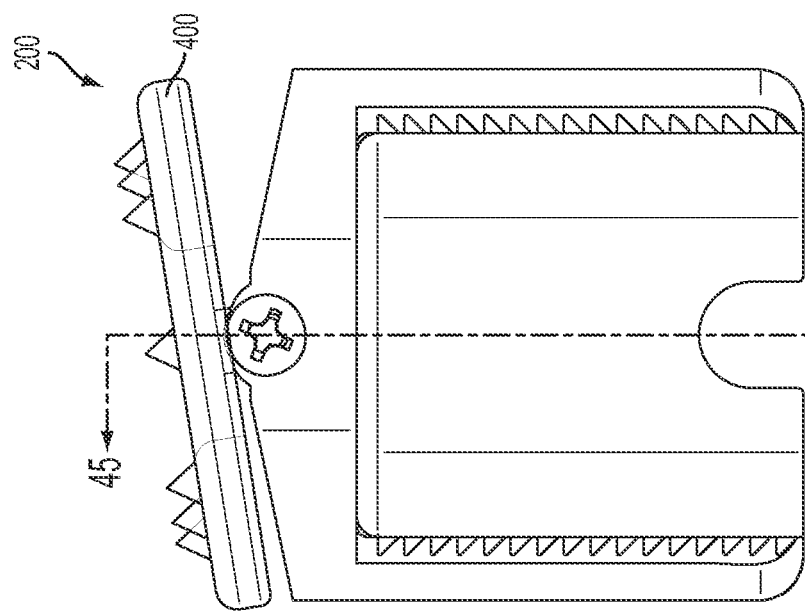
FIG. 43 is a front view of the outer housing of FIG. 39, illustrating the upper bone contact member in the angled position.

In another aspect, as shown in FIG. 32a, the respective bone contact member can comprise at least one elongate pivot member 800 configured to fit within a respective trough 810 defined in the top surface 240 of the outer housing (or the bottom surface of the inner housing). The elongate pivot member 800 can comprise a substantially cylindrical shape, but other shapes are contemplated. In one aspect at least a distal end 805 of the elongate pivot member can define a raised and/or depressed pattern 820. In this aspect, a portion of the trough 810 defines a complimentarily patterned raised and/or depressed section 825. In one aspect, the pattern is a starburst, as shown in FIG. 32a, but other complimentary patterns are contemplated. In this aspect, urging the distal end of the pivot member into engagement with the patterned portion of the trough fixes the angle of the bone contact member with respect to the respective housing. For example, a set screw 830 may be used, as shown in FIG. 37, to urge the pivot member into engagement with the patterned portion of the trough.

In still another aspect, the respective bone contact member can be locking into angular position by insertion of a wedge member 900 in the space between the bone contact member and the respective housing. FIG. 20 shows a wedge member between the upper bone contact member and the outer housing and another wedge member between the lower bone contact member and the inner housing. The wedge members can be configured in various ways to achieve the desired angle. In one aspect, the wedge member can be fixed to the VBR with a fixation device, such as a screw.

A system is presented, comprising a VBR device and a VBR expansion tool 1000. In one exemplified aspect, the VBR expansion tool 1000 comprises an actuation member 1100 coupled to a leveling member 1200. The actuation member comprises a first handle 1110 hingedly coupled to an opposed second handle 1120. The first handle comprises a proximal end 1112 configured to be held by a person's hand and a distal end 1114, with a hinge point 1130 therebetween. The second handle 1120 also comprises a proximal end 1122 configured to be held by a person's hand and a distal end 1124, with the hinge point therebetween 1130. The actuation member is configured to move from a first position where the proximal ends of the handles are at their most separated position and where the distal ends of the handles are at substantially their closest position, to a second position where the proximal ends of the handles are compressed toward one another and where the distal ends of the handles are separated. The VBR expansion tool can also comprise a compression retention member 1140 hingedly connected to a proximal end of one of the first or second handles configured to engage a catch mechanism 1145 positioned on the other handle. The compression retention member, when engaged with the catch mechanism, substantially maintains pressure on the first and second handles.

Continuing with the VBR expansion tool, the leveling member 1200 comprises an upper leveling member 1210 and a lower leveling member 1220, the two leveling members are separated by and connected by a scissor member 1250. The scissor member comprises a first scissor arm 1260 and a second scissor arm 1270. The scissor arms 1260, 1270 are pinned substantially in their middle section 1280, similar to common scissors. The proximal end 1262 of the first scissor arm 1260 is pinned to a proximal end 1212 of the upper leveling member 1210 and the distal end 1264 of the first scissor arm comprises a first pin 1266 configured to engage, in sliding relation, an elongate slot 1218 defined in the lower leveling member. Similarly, the proximal end 1272 of the second scissor arm 1270 is pinned to a proximal end 1222 of the lower leveling member 1220 and the distal end 1274 of the second scissor arm comprises a second pin 1276 configured to engage, in sliding relation, and elongate slot 1216 defined in the upper leveling member. In this fashion, as the proximal end of the upper leveling member is separated from the proximal end of the lower leveling member, the distal end of the upper leveling member is also raised and equally separated from the distal end of the lower leveling member. As can be appreciated, the relation of the arms to the leveling members can be reversed with similar results.

Figure 69:
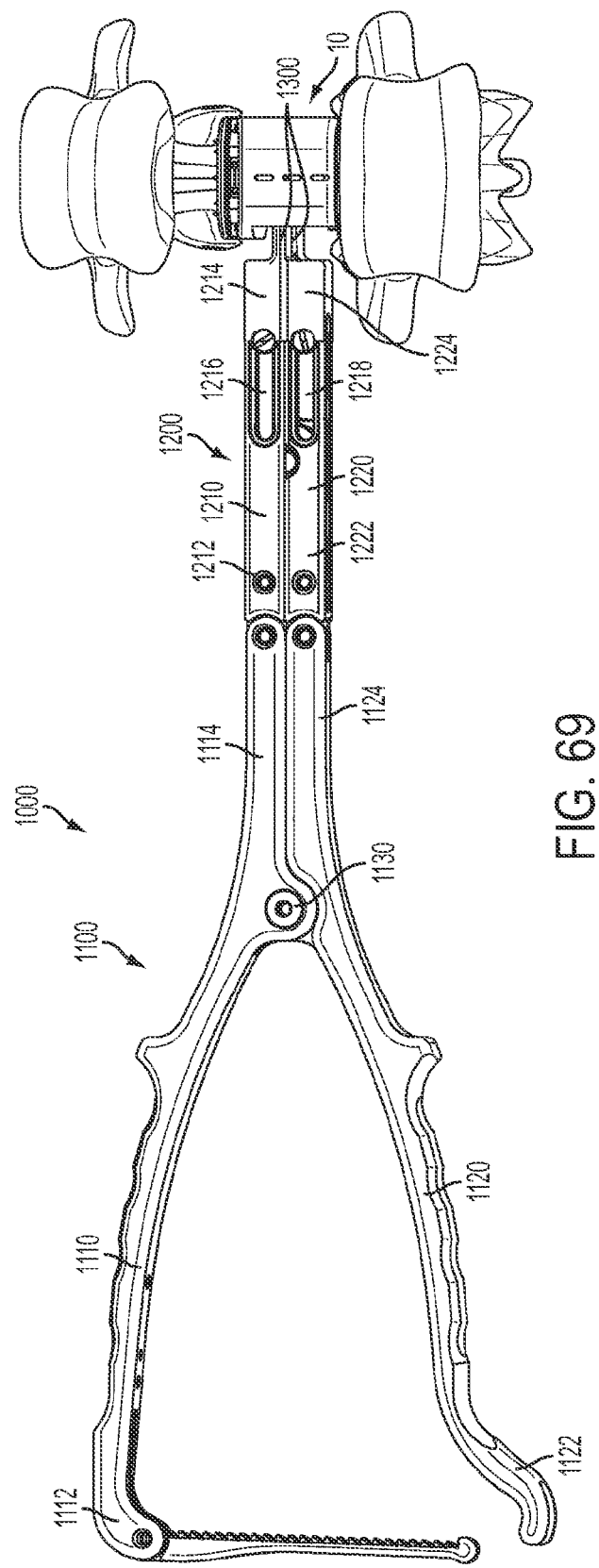
FIG. 69 is a side view of the VBR expansion tool of FIG. 68, illustrating the VBR expansion tool engaged with the VBR device in the retracted or unexpanded position.
Figure 70:
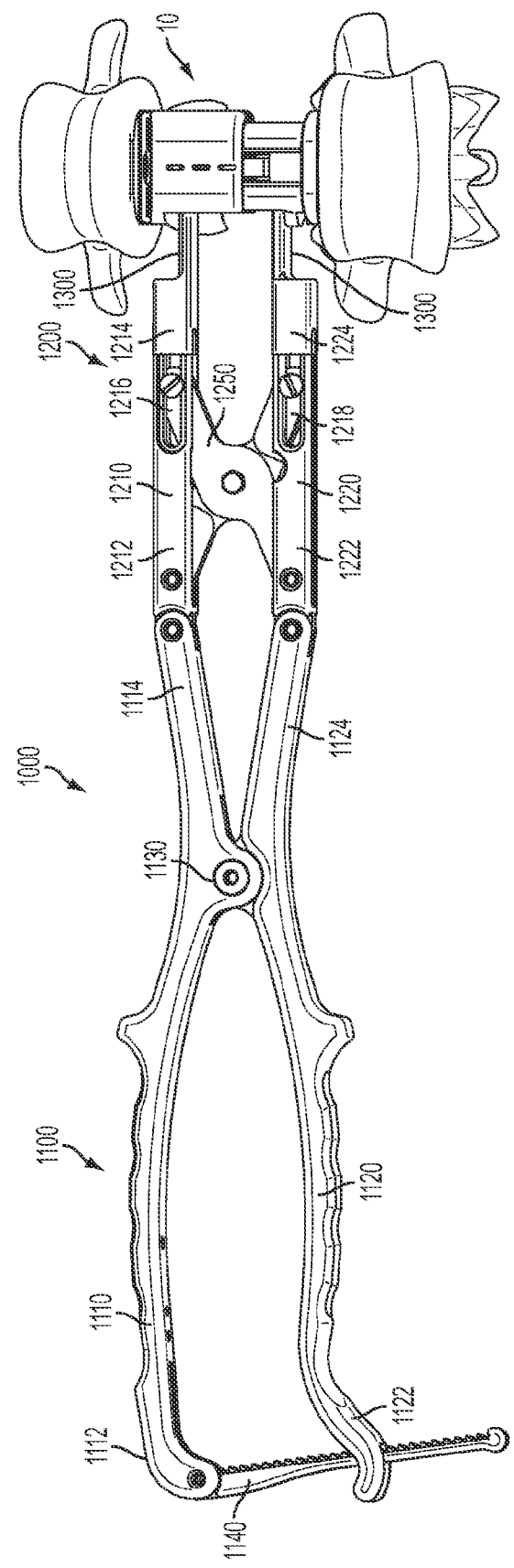
FIG. 70 is a side view of the VBR expansion tool of FIG. 68, illustrating the VBR expansion tool engaged with the VBR device after expansion.
Figure 71:
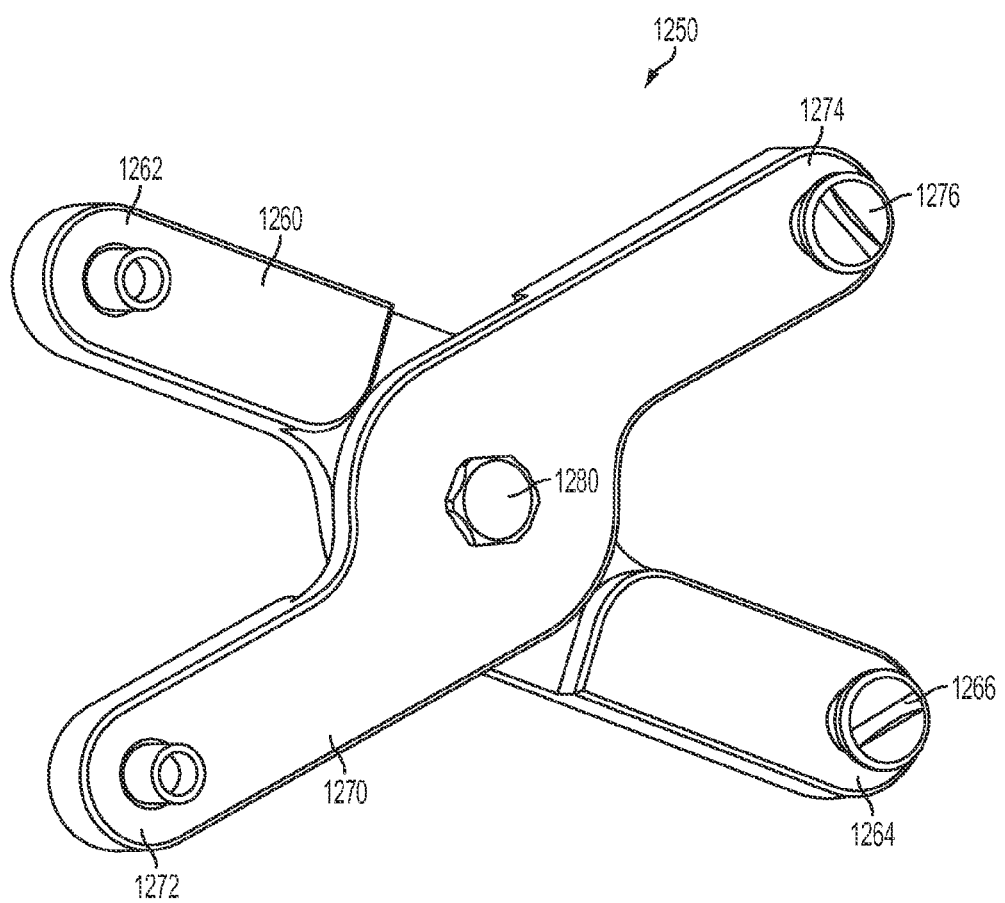
FIG. 71 is a side view of a scissor member for a VBR expansion tool.

As illustrated in FIG. 69, the distal end of the first handle 1114 can be hingedly connected to the proximal end 1214 of the upper leveling member and the distal end 1124 of the second handle can be hingedly connected to the proximal end 1222 of the lower leveling member. Additionally the distal end of the upper and lower leveling members can comprise forks 1300 to engage portions of the expandable VBR device. In use, compression of the handles of the actuation member from the first position to the second position, moves the leveling members from a position substantially adjacent one another to a separated position. By doing so, when the forks are engaged with portions of the inner and outer housings, the expandable VBR device moves from the unexpanded position to the expanded position.

A method of placing an expandable VBR into a corpectomy defect, and expanding the height of the device using a VBR expansion tool is presented. The method comprises, accessing the desired motion segment, removing the desired vertebral body, positioning the expandable VBR device in place of the removed vertebral body, expanding the expandable VBR device, and fixing the expandable VBR device in the expanded position. The method can also comprise fixing the lordotic angle of the upper and/or lower bone contact members. In another aspect, the method also comprises packing the graft cavity with bone growth promoting materials.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. A vertebral body replacement device comprising:
an outer housing defining an interior cavity and having an interior surface;
an inner housing having an exterior surface and nesting within at least a portion of the interior cavity of the outer housing, the inner housing moveable along a longitudinal direction to increase a height of the vertebral body replacement device, wherein the exterior surface of the inner housing is engageable with the interior surface of the outer housing and wherein the exterior surface of the inner housing moves from a normal, unbiased position where it is engaged with the interior surface of the outer housing, substantially preventing the outer housing from moving longitudinally with respect to the inner housing, to a biased position, where the exterior surface of the inner housing is substantially disengaged from the interior surface of the outer housing, permitting longitudinal movement of the outer housing with respect to the inner housing;

a retention member positionable within the interior cavity and removably engageable with a portion of the inner housing, wherein the retention member, when positioned in engagement with the inner housing prevents the exterior surface of the inner housing from biasing inwardly and, thus, prevents longitudinal movement of the outer housing with respect to the inner housing and contraction of the vertebral body replacement device;

an upper bone contact member having an upper bone contact surface; and a lower bone contact member having a lower bone contact surface.

2. The vertebral body replacement device of claim 1, wherein the inner housing and outer housing define a graft cavity for the placement of bone graft material.

3. The vertebral body replacement device of claim 1, wherein the upper bone contact member is pivotally connected to a portion of a top portion of the outer housing enabling the upper bone contact member to angulate in either an anterior or posterior direction.

4. The vertebral body replacement device of claim 1, wherein the lower bone contact member is pivotally connected to a portion of a lower portion of the inner housing enabling the lower bone contact member to angulate in either an anterior or posterior direction.

5. The vertebral body replacement device of claim 4, wherein at least one of the upper and lower bone contact members comprise means for locking the respective upper or lower bone contact member into a desired angular position.

6. The vertebral body replacement device of claim 5, wherein the means for locking the respective upper or lower bone contact member into a desired angular position comprises a wedge member configured to be removably positioned between the respective bone contact member and the housing to which the respective bone contact member is connected.

7. The vertebral body replacement device of claim 1, wherein at least one of the upper and lower contact surfaces define a plurality of surface protrusions configured to engage adjacent bony structure.

8. The vertebral body replacement device of claim 7, wherein the plurality of surface protrusions are spikes that can move from a undeployed state, where substantially all of the spike is beneath the respective contact surface, to a deployed state, where at least a portion of the spike extends above the respective contact surface.

9. The vertebral body replacement device of claim 8, further comprising means for deploying the spikes.

10. A method for replacing a vertebral body comprising the steps of:
accessing a desired motion segment;
removing a desired vertebral body;
positioning an expandable VBR device in place of the removed vertebral body;
expanding the expandable VBR device; and
fixing the expandable VBR device in the expanded position; and
wherein the VBR device comprises:
an outer housing defining an interior cavity and having an interior toothed surface;
an inner housing having an exterior surface and nesting within at least a portion of the interior cavity of the outer housing, the inner housing moveable along a longitudinal direction to increase a height of the VBR device, wherein the exterior surface of the inner housing is engageable with the interior surface of the outer housing and wherein the exterior surface of the inner housing moves from a normal, unbiased position where it is engaged with the interior surface of the outer housing, substantially preventing the outer housing from moving longitudinally with respect to the inner housing, to a biased position, where the exterior surface of the inner housing is substantially disengaged from the interior surface of the outer housing, permitting longitudinal movement of the outer housing with respect to the inner housing;
a retention member removably engageable with a portion of the inner housing, wherein the retention member, when positioned in engagement with the inner housing, prevents the exterior surface of the inner housing from biasing inwardly and, thus, prevents longitudinal movement of the outer housing with respect to the inner housing and contraction of the VBR device;
an upper bone contact member having an upper bone contact surface; and
a lower bone contact member having a lower bone contact surface.

11. The method of claim 10, wherein the inner housing and outer housing define a graft cavity for the placement of bone graft material and the method further comprises the step of packing the graft cavity with bone growth promoting materials.

12. The method of claim 10, wherein the upper bone contact member is pivotally connected to a portion of a top portion of the outer housing enabling the upper bone contact member to angulate in either an anterior or posterior direction, and the lower bone contact member is pivotally connected to a portion of a lower portion of the inner housing enabling the lower bone contact member to angulate in either an anterior or posterior direction, the method further comprising the step of fixing a lordotic angle of at least one of the upper and lower bone contact members.

13. A system for replacing a vertebral body comprising:
an expandable VBR device comprising:
an outer housing defining an interior cavity and having an interior surface;
an inner housing having an exterior surface and nesting within at least a portion of the interior cavity of the outer housing, the inner housing moveable along a longitudinal direction to increase a height of the expandable VBR device, wherein the exterior surface of the inner housing is engageable with the interior surface of the outer housing and wherein the exterior surface of the inner housing moves from a normal, unbiased position where it is engaged with the interior surface of the outer housing, substantially preventing the outer housing from moving longitudinally with respect to the inner housing, to a biased position, where the exterior surface of the inner housing is substantially disengaged from the interior surface of the outer housing, permitting longitudinal movement of the outer housing with respect to the inner housing;
a retention member removably engageable with a portion of the inner housing, wherein the retention member, when positioned in engagement with the inner housing, prevents the exterior surface of the inner housing from biasing inwardly and, thus, prevents longitudinal movement of the outer housing with respect to the inner housing and contraction of the expandable VBR device;

an upper bone contact member having an upper bone contact surface: and a lower bone contact member having a lower bone contact surface; and a VBR expansion tool.

14. The system of claim 13, wherein the inner housing and outer housing define a graft cavity for the placement of bone graft material.

15. The system of claim 13, wherein the upper bone contact member is pivotally connected to a portion of a top portion of the outer housing enabling the upper bone contact member to angulate in either an anterior or posterior direction and the lower bone contact member is pivotally connected to a portion of a lower portion of the inner housing enabling the lower bone contact member to angulate in either an anterior or posterior direction.

16. The system of claim 15, wherein the VBR expansion tool comprises:

an actuation member having a first handled and an opposed second handle, wherein the first and second handles are hingedly coupled at a hinge point, the hinge point being positioned between a proximal end and a distal end of each of the first and second handles; and a leveling member coupled to the actuation member, the leveling member having an upper leveling member and a lower leveling member, the upper and lower leveling members separated by and connected by a scissor member, wherein the scissor member comprises a first scissor arm and a second scissor arm pinned substantially in their middle section and wherein the proximal end of the first scissor arm is pinned to a proximal end of the upper leveling member and the distal end of the first scissor arm comprises a pin configured to engage, in sliding relation, an elongate slot defined in the lower leveling member, and wherein the proximal end of the second scissor arm is pinned to a proximal end of the lower leveling member and the distal end of the second scissor arm comprises a pin configured to engage, in sliding relation, and elongate slot defined in the upper leveling member such that, as the proximal end of the upper leveling member is separated from the proximal end of the lower leveling member, the distal end of the upper leveling member is also raised and equally separated from the distal end of the lower leveling member.

17. The system of claim 16, wherein the distal end of the first handle is hingedly connected to the proximal end of the upper leveling member and the distal end of the second handle can be hingedly connected to the proximal end of the lower leveling member.

18. The system of claim 16, wherein the distal end of the upper and lower leveling members each comprise forks to engage portions of the expandable VBR device, whereby, in use, compression of the handles of the actuation member from a first, separated position to the second, compressed position, moves the leveling members from a position substantially adjacent one another to a separated position.

\* \* \* \* \*